United States Patent [19]

Jung et al.

[11] Patent Number: 5,571,805
[45] Date of Patent: *Nov. 5, 1996

[54] ANTIBIOTIC COMPOUNDS

[75] Inventors: Frederic H. Jung, Rilly la Montagne; Alain M. Bertrandie, Cormontreuil, both of France; Ronald H. B. Galt, Cheshire, England

[73] Assignee: Zeneca Limited, London, United Kingdom

[*] Notice: The term of this patent shall not extend beyond the expiration date of Pat. No. 5,478,820.

[21] Appl. No.: 302,394

[22] Filed: Sep. 8, 1994

Related U.S. Application Data

[63] Continuation of Ser. No. 37,171, Mar. 26, 1993, abandoned.

[30] Foreign Application Priority Data

Mar. 26, 1992 [EP] European Pat. Off. .............. 92400837
Mar. 26, 1992 [EP] European Pat. Off. .............. 92400839
Oct. 2, 1992 [EP] European Pat. Off. .............. 92402700

[51] Int. Cl.⁶ ...................... A61K 31/40; C07D 487/04
[52] U.S. Cl. ........................................... 514/210; 540/350
[58] Field of Search ............................ 514/210; 540/350

[56] References Cited

FOREIGN PATENT DOCUMENTS 0017992 10/1980 European Pat. Off. .
0126587 11/1984 European Pat. Off. .
0160391 11/1985 European Pat. Off. .
0182213 5/1986 European Pat. Off. .
9217481 10/1992 WIPO .

*Primary Examiner*—Rebecca Cook
*Attorney, Agent, or Firm*—Cushman Darby & Cushman, L.L.P.

[57] ABSTRACT

The present invention relates to carbapenems and provides a compound of the formula (I)

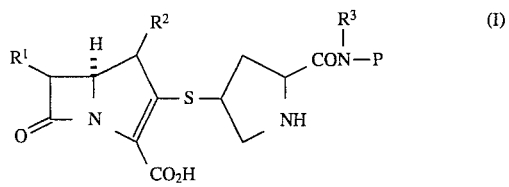

wherein:
$R^1$ is 1-hydroxyethyl, 1-fluoroethyl or hydroxyethyl;
$R^2$ is hydrogen or $C_{1-4}$alkyl;
$R^3$ is hydrogen or $C_{1-4}$alkyl;
P is of the formula (IA), (IB) or (IC)

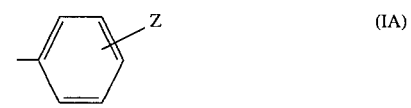

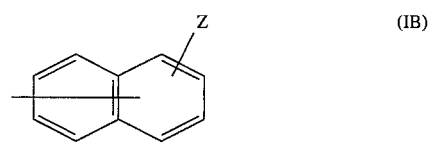

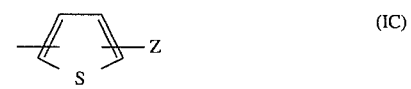

and in the formula (IB) the naphthyl group may be bonded to the nitrogen of the linking carbamoyl group at either ring; Z is carboxy, sulfonic acid, sulfinic acid, $C_{1-4}$alkanamidosulfonyl ($-SO_2NHCOC_{1-3}$alkyl), benzamidosulfonyl, $C_{1-4}$alkylsulfonylcarbamoyl ($-CONHSO_2C_{1-4}$alkyl), phenylsulfonylcarbamoyl, $C_{1-4}$alkoxy carbamoyl, hydroxycarbamoyl, sulfoamino, $\underline{N}$—$C_{1-4}$alkanesulfonamido, cyanocarbamoyl, cyanosulfamoyl, tetrazol-5-yl, 3-hydroxyisoxazol-4-yl and 3-hydroxyisoxazol-5-yl;

and P is optionally further substituted provided that when P is of the formula (IA) or (IC), Z is not carboxy; or a pharmaceutically acceptable salt or in vivo hydrolysable ester thereof. Processes for their preparation, intermediates in their preparation, their use as therapeutic agents and pharmaceutical compositions containing them are also described.

42 Claims, No Drawings

ANTIBIOTIC COMPOUNDS

This is a continuation of application Ser. No. 08/037,171, filed on Mar. 26, 1993, which was abandoned upon the filing hereof.

The present invention relates to carbapenems and in particular to such compounds containing a thienyl, phenyl or naphthyl group substituted with certain acidic groups. This invention further relates to processes for their preparation, to intermediates in their preparation, to their use as therapeutic agents and to pharmaceutical compositions containing them. The compounds of this invention are antibiotics and can be used in the treatment of any disease that is conventionally treated with antibiotics for example in the treatment of bacterial infection in mammals including humans.

Carbapenems were first isolated from fermentation media in 1974 and were found to have broad spectrum antibacterial activity. Since this discovery substantial investigations have been made into new carbapenem derivatives and many hundreds of patents and scientific papers have been published.

The first, and so far the only, carbapenem to be commercially marketed is imipenem (N-formimidoyl thienamycin). This compound has a broad spectrum of antibacterial activity.

The present invention provides compounds with a broad spectrum of antibacterial activity including against both Gram positive and negative, aerobic and anaerobic bacteria. They exhibit good stability to beta-lactamases. In addition representative compounds of this invention exhibit favourable pharmacokinetics.

The carbapenem derivatives referred to herein are named in accordance with the generally accepted semi-systematic nomenclature:

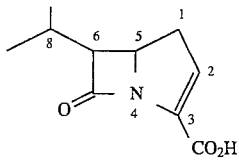

Accordingly the present invention provides a compound of the formula (I)

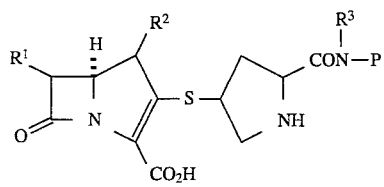

wherein:
$R^1$ is 1-hydroxyethyl, 1-fluoroethyl or hydroxymethyl;
$R^2$ is hydrogen or $C_{1-4}$alkyl;
$R^3$ is hydrogen or $C_{1-4}$alkyl;
P is of the formula (IA), (IB) or (IC)

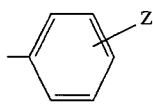

and in the formula (IB) the naphthyl group may be bonded to the nitrogen of the linking carbamoyl group at either ring; Z is carboxy, sulfonic acid, sulfinic acid, $C_{1-4}$alkanamidosulfonyl ($-SO_2NHCOC_{1-3}$alkyl), benzamidosulfonyl, $C_{1-4}$alkylsulfonylcarbamoyl ($-CONHSO_2C_{1-4}$alkyl), phenylsulfonylcarbamoyl, $C_{1-4}$alkoxy carbamoyl, hydroxycarbamoyl, sulfoamino, $\underline{N}$—$C_{1-4}$alkanesulfonamido, cyanocarbamoyl, cyanosulfamoyl, tetrazol-5-yl, 3-hydroxyisoxazol-4-yl and 3-hydroxyisoxazol-5-yl;

and P is optionally further substituted by one or two substituents selected from halo, cyano, $C_{1-4}$alkyl, nitro, hydroxy, carboxy, $C_{1-4}$alkoxy, trifluoromethyl, $C_{1-4}$alkoxycarbonyl, amino, $C_{1-4}$alkylamino, di-$C_{1-4}$alkylamino, sulfonic acid, $C_{1-4}$alkylS(O)$_n$- (wherein n is 0–2), $C_{1-4}$alkanoylamino, $C_{1-4}$alkanoyl($\underline{N}$—$C_{1-4}$alkyl)amino, carbamoyl, $C_{1-4}$alkylcarbamoyl and di-$C_{1-4}$alkylcarbamoyl;

provided that when P is a ring of the formula (IA) or (IC) and Z is either sulfonic acid or $\underline{N}$—$C_{1-4}$alkanesulfonamido, the ring is not substituted by carboxy; and when P is of the formula (IA) or (IC), Z is not carboxy;

or a pharmaceutically acceptable salt or in vivo hydrolysable ester thereof.

The term alkyl includes all straight and branched chain structures, for example, $C_{1-4}$alkyl includes $\underline{n}$-butyl and 2-methylpropyl.

Preferably $R^1$ is 1-hydroxyethyl.

$R^2$ is hydrogen or $C_{1-4}$alkyl for example methyl, ethyl, $\underline{n}$-propyl, 1-methylethyl and $\underline{n}$-butyl.

Preferably $R^2$ is hydrogen or methyl. In particular $R^2$ is methyl.

$R^3$ is hydrogen or $C_{1-4}$alkyl for example methyl, ethyl, n-propyl, isopropyl and n-butyl.

Preferably $R^3$ is hydrogen or methyl. In particular $R^3$ is hydrogen.

Preferably Z is sulfonic acid, tetrazol-5-yl $C_{1-4}$alkylsulfonylcarbamoyl, phenylsulfonylcarbamoyl or cyanocarbamoyl.

Most preferably Z is sulfonic acid or tetrazol-5-yl.

In particular Z is sulfonic acid.

In one aspect P is of the formula (IA) or (IB) and Z and optional substituents on P are as hereinbefore defined, provided that when P is of the formula (IB), Z is not carboxy.

In another aspect P is of the formula (IB), optional substituents on P are as hereinbefore defined and Z is carboxy.

In a further aspect P is of the formula (IC) and Z and optional substituents on P are as hereinbefore defined.

Preferably, when P is optionally substituted, the optional substituents are selected from halo, cyano, $C_{1-4}$alkyl, nitro, hydroxy, $C_{1-4}$alkoxy, carbamoyl, amino and trifluoromethyl.

Suitable substituents for P include, for example:

| | |
|---|---|
| for halo: | fluoro, chloro, bromo and iodo; |
| for $C_{1-4}$alkyl: | methyl, ethyl, propyl, 1-methylethyl, butyl and 2-methylpropyl; |
| for $C_{1-4}$alkoxy: | methoxy, ethoxy, propoxy, 1-methylethoxy, butoxy and 2-methylpropoxy; |
| for $C_{1-4}$alkylcarbamoyl: | methylcarbamoyl, ethylcarbamoyl and propylcarbamoyl; |
| for di-$C_{1-4}$alkylcarbamoyl: | dimethylcarbamoyl and diethylcarbamoyl; |
| for $C_{1-4}$alkylamino: | methylamino, ethylamino and propylamino; |
| for di-$C_{1-4}$alkylamino: | dimethylamino, diethylamino and methylethylamino; |
| for $C_{1-4}$alkylS(O)$_n$-: | methylthio, methylsulfinyl and methylsulfonyl; |
| for $C_{1-4}$alkanoylamino: | acetamido and propionamido; |
| for $C_{1-4}$alkoxycarbonyl: | methoxycarbonyl, ethoxycarbonyl and propoxycarbonyl; |
| for $C_{1-4}$alkanoyl(N-$C_{1-4}$alkyl)amino: | N-methylacetamido and N-ethylacetamido. |

The present invention covers all epimeric, diastereoisomeric and tautomeric forms of the compounds of the formula (I) wherein the absolute stereochemistry at the 5-position is as illustrated in formula (I). When a bond is represented as a wedge, this indicates that in three dimensions the bond would be coming forward out of the paper and when a bond is represented as hatched, this indicates that in three dimensions the bond would be going back into the paper. The compounds of the formula (I) have a number of other stereocentres, namely: within the group $R^1$ (when $R^1$ is 1-hydroxyethyl or 1-fluoroethyl); at the 6-position; at the 1-position (when $R^2$ is $C_{1-4}$alkyl); and at the 2' and 4' positions in the pyrrolidine ring:

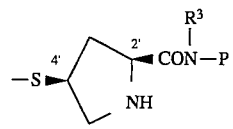
(II)

Preferred compounds are those in which the beta-lactam protons are in trans configuration with respect to one another. When $R^1$ is 1-hydroxyethyl or 1-fluoroethyl it is preferred that the 8-substituent has the R-configuration. Thus a preferred class of compounds is that of the formula (III):

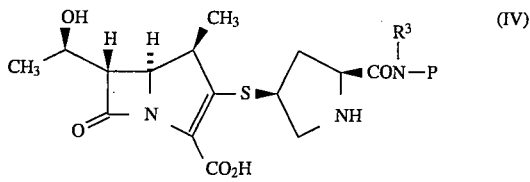
(III)

and pharmaceutically acceptable salts and in vivo hydrolysable esters thereof, wherein P, $R^2$, $R^3$ and optional substituents on P are as hereinbefore defined.

When $R^2$ is $C_{1-4}$alkyl, for example methyl, it is preferred that the compound is in the form of the 1R configuration.

Preferred compounds are those in which the pyrrolidine ring has the following absolute stereochemistry at the 2'- and 4'-positions:

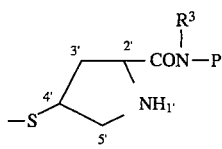

A suitable class of compounds of the present invention is that of the formula (IV):

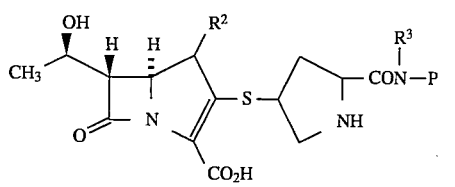
(IV)

and pharmaceutically acceptable salts and in vivo hydrolysable esters thereof; wherein P, $R^3$ and optional substituents on P are as defined hereinbefore in formula (I).

In another aspect a suitable class of compounds are the compounds of the formula (IV) wherein $R^3$ is hydrogen, methyl or ethyl; and Z on P and optional substituents on P are as defined hereinabove in formula (I).

A particular class of compounds of the present invention is that of the formula (IV) wherein:

Z is sulfonic acid; P is of the formula (IA) or (IB) and is optionally further substituted by one or two substituents selected from methyl, ethyl, hydroxy, cyano, fluoro, chloro, bromo, nitro, methoxy, ethoxy, carbamoyl and propoxy; and $R^3$ is as hereinbefore defined in formula (I).

In another aspect a suitable class of compounds is that of the compounds of the formula (IV) wherein $R^3$ is hydrogen, methyl or ethyl and Z is carboxy, sulfonic acid, tetrazol-5-yl, $C_{1-4}$alkylsulfonylcarbamoyl, phenylsulfonylcarbamoyl or cyanocarbamoyl; and optional substituents on P are as hereinbefore defined.

In yet another aspect a suitable class of compounds is that of the compounds of the formula (IV) wherein Z is carboxy, sulfonic acid, tetrazol-5-yl, $C_{1-4}$alkylsulfonylcarbamoyl, phenylsulfonylcarbamoyl or cyanocarbamoyl; and P is optionally further substituted by one or two substituents selected from methyl, ethyl, hydroxy, cyano, fluoro, chloro, bromo, carbamoyl, nitro, methoxy, ethoxy and propoxy; and $R^3$ and P are as defined hereinbefore in formula (I).

A preferred class of compounds of the present invention is that of the formula (IV) wherein:

$R^3$ is hydrogen;

and Z is carboxy, sulfonic acid, tetrazol-5-yl, methylsulfonylcarbamoyl, phenylsulfonylcarbamoyl or cyanocarbamoyl; and P is optionally further substituted by one or two substituents selected from methyl, hydroxy and methoxy.

Another preferred class of compounds of the present invention that of the formula (IV) wherein: $R^3$ is hydrogen; and Z is carboxy, sulfonic acid, tetrazol-5-yl, methylsulfonylcarbamoyl, phenylsulfonylcarbamoyl or cyanocarbamoyl; and P is not further substituted.

Particular compounds of the present invention are, for example, the following compounds of the formula (IV):

(1R,5S,6S,8R,2'S,4'S)-2-(2-(3-sulfophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(3-methylsulfonylcarbamoylphenylcarbamoyl)pyrrolidin-4-ylthio)-4-ylthio-6-(1-hydroxyethyl)-1-methylcarbapenem-3-carboxylic acid;

(1R,5S,6S,8R,2'S,4'S)-2-(2-(2-(3-1H-tetrazol-5-yl)phenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-hydroxy-5-sulfophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-methoxy-5-methyl-4-sulfophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(3-phenylsulfonylcarbamoylphenylcarbamoyl)pyrrolidin4-ylthio)-6-(1-hydroxyethyl)-1-methylcarbapenem-3-carboxylic acid;

(1R,5S,6S,8R,2'S,4'S)-2-(2-(2-methylsulfonylcarbamoyl-5-thienyl carbamoyl)pyrrolidin-4-ylthio)-6-(1-hydroxyethyl)-1-methylcarbapenem-3-carboxylic acid;

(1R,5S,6S,8R,2'S,4'S)-2-(2-(2-cyanocarbamoyl-5-thienylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-sulfo-5-thienylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(1-carboxy-3-naphthylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-3-naphthylcarbamoyl)pyrrolidin- 4-ylthio)-6-(1-hydroxyethyl)-1-methylcarbapenem-3-carboxylic acid;

(1R,5S,6S,8R,2'S,4'S)-2-(2-(2-sulfophenylcarbamoyl)pyrrolidin-4-ylthio)-6-(1-hydroxyethyl)-1-methylcarbapenem-3-carboxylic acid; and (1R,5S,6S,8R,2'S,4'S)-2-(2-(2-hydroxy-4-sulfo-1-naphthylcarbamoyl)pyrrolidin-4-ylthio)-6-(1-hydroxyethyl)-1-methylcarbapenem-3-carboxylic acid;

and pharmaceutically acceptable salts and in vivo hydrolysable esters thereof.

Suitable pharmaceutically acceptable salts include acid addition salts such as hydrochloride, hydrobromide, citrate, maleate and salts formed with phosphoric and sulphuric acid. In another aspect suitable salts are base salts such as an alkali metal salt for example sodium or potassium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine or aminoacids, for example, lysine.

For the avoidance of doubt there may be one, two, three or four salt-forming cations dependent on the number of carboxylic acid functions and valency of said cations.

Preferred pharmaceutically acceptable salts are sodium and potassium salts. However, to facilitate isolation of the salt during preparation, more insoluble salts may be preferred.

In vivo hydrolysable esters are those pharmaceutically acceptable esters that hydrolyse in the human body to produce the parent hydroxy or carboxy compound. Such esters can be identified by administering, eg. intravenously to a test animal, the compound under test and subsequently examining the test animal's body fluids. Suitable in vivo hydrolysable ester forming groups for hydroxy include aceteyl, propionyl, pivaloyl, $C_{1-4}$alkoxycarbonyl for example ethoxycarbonyl and phenylacetyl. Suitable in vivo hydrolysable esters for carboxy include $C_{1-6}$alkoxymethyl esters for example methoxymethyl; $C_{1-6}$alkanoyloxymethyl esters for example pivaloyloxymethyl; $C_{3-8}$cycloalkoxycarbonyloxy$C_{1-6}$alkyl, for example 1-cyclohexyloxycarbonyloxyethyl; 1,3-dioxolen-2-onylmethyl esters for example 5-methyl-1,3-dioxolen-2-onylmethyl; phthalidyl esters and $C_{1-6}$alkoxycarbonyloxyethyl esters for example 1-methoxycarbonyloxyethyl and may be formed at any carboxy group in the compounds of this invention.

In order to use a compound of the formula (I) or a pharmaceutically acceptable salt or in vivo hydrolysable ester thereof for the therapeutic treatment of mammals including humans, in particular in treating infection, it is normally formulated in accordance with standard pharmaceutical practice as a pharmaceutical composition.

Therefore in another aspect the present invention provides a pharmaceutical composition which comprises a compound of the formula (I) or a pharmaceutically acceptable salt or in vivo hydrolysable ester thereof and a pharmaceutically acceptable carrier.

The compounds of the present invention may be formulated as dry powder filled vials, which may contain the compound of the present invention alone or as a dry blended mixture. For example an acidic compound of the present invention may be dry blended with an alkali metal carbonate or bicarbonate. Freeze dried formulations of compounds of the present invention, alone or as a mixture with standard excipients, are possible. Standard excipients include structure formers, cryoprotectants and pH modifiers, such as, mannitol, sorbitol, lactose, glucose, sodium chloride, dextran, sucrose, maltose, gelatin, bovine serum albumin (BSA), glycine, mannose, ribose, polyvinylpyrrolidine (PVP), cellulose derivatives, glutamine, inositol, potassium glutamate, erythritol, serine and other amino acids and buffer agents e.g. disodium hydrogen phosphate and potassium citrate.

The pharmaceutical compositions of this invention may be administered in standard manner for the disease condition that it is desired to treat, for example by oral, rectal or parenteral administration. For these purposes the compounds of this invention may be formulated by means known in the art into the form of, for example, tablets, capsules, aqueous or oily solutions or suspensions, emulsions, dispersible powders, suppositories and sterile injectable aqueous or oily solutions or suspensions.

In addition to the compounds of the present invention the pharmaceutical composition of this invention may also contain, or be co-administered with, one or more known drugs selected from other clinically useful antibacterial agents (for example other beta-lactams or aminoglycosides), inhibitors of beta-lactamase (for example clavulanic acid), renal tubular blocking agents (e.g. probenecid) and inhibitors of metabolising enzymes (for example inhibitors of dehydropeptidases, for example Z-2-acylamino-3-substituted propenoates such as cilastatin) and N-acylated amino acids such as betamipron (also see EP-A-178911).

A suitable pharmaceutical composition of this invention is one suitable for oral administration in unit dosage form, for example a tablet or capsule which contains between 100 mg and 1 g of the compound of this invention.

A preferred pharmaceutical composition of the invention is one suitable for intravenous, subcutaneous or intramuscular injection, for example a sterile injectable composition containing between 1 and 50% w/w of the compound of this invention.

Specific examples of compositions, which are constituted as a 1% solution in water, freeze dried and may be made up by adding 0.9% aqueous sodium chloride solution to give the required concentration, preferably 1 mg–10 mg/ml, are as follows:

| Composition 1 | |
|---|---|
| Compound of Example 1 | 50 mg |
| Composition 2 | |
| Compound of Example 1 | 50 mg |
| Glycine | 31 mg |

Further specific examples of compositions are as above, but where the compound of example 1 is replaced by any one of examples 2 to 12.

The pharmaceutical compositions of the invention will normally be administered to man in order to combat infections caused by bacteria, in the same general manner as that employed for imipenem due allowance being made in terms of dose levels for the pharmacokinetics of the compound of the present invention relative to the clinical use of imipenem. Thus each patient will receive a daily intravenous, subcutaneous or intramuscular dose of 0.05 to 5 g, and preferably 0.1 to 2.5 g, of the compound of this invention, the composition being administered 1 to 4 times per day, preferably 1 or 2 times a day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose. Thus a suitable daily oral dose is 0.05 to 5 g. of the compound of this invention, the composition being administered 1 to 4 times per day.

In a further aspect the present invention provides a process for preparing the compounds of the formula (I) or a pharmaceutically acceptable salt or in vivo hydrolysable ester thereof which process comprises deprotecting a compound of the formula (V) wherein $P^1$ is optionally further substituted as for P in formula (I):

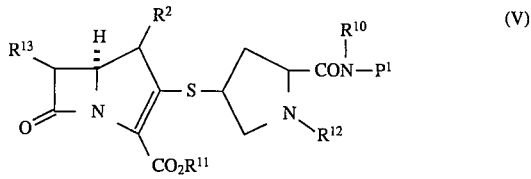

wherein $R^2$ is as hereinbefore defined; $R^{10}$ is a group $R^3$ or an amino protecting group; $R^{13}$ is a group $R^1$, protected hydroxymethyl or 1-(protected hydroxy)ethyl; $R^{11}$ is hydrogen or a carboxy protecting group; $R^{12}$ is hydrogen or an amino protecting group:

$p^1$ is of the formula (ID), (IE) or (IF)

and in formula (IE) the naphthyl group may be bonded to the nitrogen of the linking carbamoyl group at either ring;

$R^{18}$ is a group Z or a protected Z group and wherein any optional substituent on $p^1$ is optionally protected; and wherein at least one protecting group is present; and thereinafter if necessary;

(i) forming a pharmaceutically acceptable salt, (ii) esterifying to form an in vivo hydrolysable ester.

Protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

The compounds of the formula (V) are novel and form another aspect of the invention.

Specific examples of protecting groups are given below for the sake of convenience, in which "lower" signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

Examples of hydroxy protecting groups include lower alkenyl groups (eg allyl); lower alkanoyl groups (eg acetyl); lower alkoxycarbonyl groups (eg t-butoxycarbonyl); lower alkenyloxycarbonyl groups (eg allyloxycarbonyl); aryl lower alkoxycarbonyl groups (eg benzoyloxycarbonyl, p-methoxybenzyloxycarbonyl, o-nitrobenzyloxycarbonyl, p-nitrobenzyloxycarbonyl); tri lower alkylsilyl (eg trimethylsilyl, t-butyldimethylsilyl); diaryl(lower alkyl)silyl (eg t-butyldiphenylsilyl) and aryl lower alkyl (eg benzyl) groups.

Examples of amino protecting groups include formyl, aralkyl groups (eg benzyl and substituted benzyl, eg p-methoxybenzyl, nitrobenzyl and 2,4-dimethoxybenzyl, and triphenylmethyl); di-p-anisylmethyl and furylmethyl groups; lower alkoxycarbonyl (eg t-butoxycarbonyl); lower alkenyloxycarbonyl (eg allyloxycarbonyl); aryl lower alkoxycarbonyl groups (eg benzyloxycarbonyl, p-methoxybenzyloxycarbonyl, o-nitrobenzyloxycarbonyl, p-nitrobenzyloxycarbonyl); trialkylsilyl (eg trimethylsilyl and t-butyldimethylsilyl); diaryl(lower alkyl)silyl (eg t-butyldiphenylsilyl); alkylidene (eg methylidene); benzylidene and substituted benzylidene groups.

Methods appropriate for removal of hydroxy and amino protecting groups include, for example, acid-, base-, metal- or enzymically-catalysed hydrolysis, for groups such as p-nitrobenzyloxycarbonyl, hydrogenation and for groups such as o-nitrobenzyloxycarbonyl, photolytically.

A carboxy protecting group may be the residue of an ester-forming aliphatic or araliphatic alcohol or of an ester-forming silanol (the said alcohol or silanol preferably containing 1–20 carbon atoms).

Examples of carboxy protecting groups include straight or branched chain (1–12C)alkyl groups (eg isopropyl, t-butyl); lower alkoxy lower alkyl groups (eg methoxymethyl, ethoxymethyl, isobutoxymethyl); lower aliphatic acyloxy lower alkyl groups, (eg acetoxymethyl, propionyloxymethyl, butyryloxymethyl, pivaloyloxymethyl); lower alkoxycarbonyloxy lower alkyl groups (eg 1-methoxycarbonyloxyethyl, 1-ethoxycarbonyloxyethyl); aryl lower alkyl groups (eg p-methoxybenzyl, o-nitrobenzyl, p-nitrobenzyl, benzhydryl and phthalidyl); tri(lower alkyl)silyl groups (eg trimethylsilyl and t-butyldimethylsilyl); tri(lower alkyl)silyl lower alkyl groups (eg trimethylsilylethyl); diaryl(lower alkyl)silyl groups (eg t-butyldiphenylsilyl); and (2–6C)alkenyl groups (eg allyl and vinylethyl).

Methods particularly appropriate for the removal of carboxyl protecting groups include for example acid-, base-, metal- or enzymically-catalysed hydrolysis, for groups such as p-nitrobenzyloxycarbonyl, hydrogenation and for groups such as o-nitrobenzyloxy carbonyl, photolytically.

Preferred protecting groups for carboxy and hydroxy groups in compounds of the formula (I) are the groups allyl and p-nitrobenzyl. A preferred method for removal of the allyl group is by palladium catalysis using tetrakis(triphenylphosphine)palladium and Meldrum's acid, in DMF or a dipolar aprotic solvent tetrahydrofuran mixture, such as dimethylsulphoxide/tetrahydrofuran or 1,3-dimethyl-2-oxotetrahydropyrimidine/tetrahydrofuran, or an alcohol/tetrahydrofuran mixture such as isopropanol/tetrahydrofuran or ethanol/tetrahydrofuran, preferably at ambient temperature. Alternatively, methylaniline may be used in place of Meldrum's acid, in dichloromethane. These conditions allow isolation of the product by precipitation of the sodium salt on the addition of a sodium salt such as sodium 2-ethylhexanoate.

A preferred method for removal of the p-nitrobenzyl group is hydrogenation using a palladium catalyst.

In another aspect of the present invention the compounds of the formulae (I) and (V) may be prepared by a) reacting compounds of the formulae (VI) and (VII):

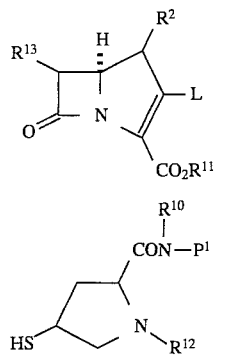

wherein $p^1$, $R^2$, $R^{10}$, $R^{11}$, $R^{12}$ and $R^{13}$ are as hereinbefore defined, optional substituents on $P^1$ are as hereinbefore defined and L is a leaving group, or b) cyclising a compound of the formula (VIII):

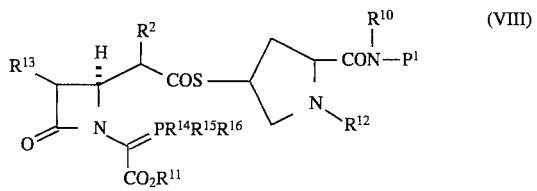

wherein $p^1$, $R^2$, $R^{10}$, $R^{11}$, $R^{12}$ and $R^{13}$ are as hereinbefore defined optional substituents on $p^1$ are as hereinbefore defined and $R^{14}$, $R^{15}$ and $R^{16}$ are independently selected from $C_{1-6}$alkoxy, aryloxy, di-$C_{1-6}$alkylamino and diarylamino or any two of $R^{14}$–$R^{16}$ represent o-phenylenedioxy or one of $R^{14}$–$R^{16}$ is $C_{1-4}$alkyl, allyl, benzyl or phenyl and the other two values are independently selected from $C_{1-4}$alkyl, trifluoromethyl or phenyl, wherein any phenyl group is optionally substituted with $C_{1-3}$alkyl or $C_{1-3}$alkoxy; and wherein any functional group is optionally protected and thereinafter if necessary:

(i) removing any protecting groups;
(ii) forming a pharmaceutically acceptable salt;
(iii) esterifying to form an in vivo hydrolysable ester.

Suitably in the compound of the formula (VI), L is the reactive ester of a hydroxy group such as a sulfonate (for example $C_{1-6}$alkanesulfonyloxy, trifluoromethanesulfonyloxy, benzenesulfonyloxy, toluenesulfonyloxy), a phosphoric ester (for example a diarylphosphoric ester such as diphenylphosphoric ester) or L is a halide (for example chloride). In an alternative L is a sulfoxide for example —SOCH=CH—NHCOCH$_3$ which may be readily displaced. Preferably L is diphenylphosphoric ester (—OP(O)(OPh)$_2$).

Compounds of the formula (VI) and their preparation are well known in the carbapenem literature, for example see EP-A-126587, EP-A-160391, EP-A-243686 and EP-A-343499.

The reaction between the compounds of the formulae (VI) and (VII) is typically performed in the presence of a base such as an organic amine for example di-isopropylethylamine or an inorganic base for example an alkali metal carbonate such as potassium carbonate. The reaction is conveniently performed at a temperature between –25° C. and ambient, suitable at about 0° C. The reaction is generally performed in an organic solvent such as acetonitrile or dimethylformamide. The reaction is generally performed in a manner similar to that described in the literature for similar reactions.

The compounds of the formula (VII) are novel and form another aspect of the present invention.

The compounds of the formula (VII) may be prepared by the deprotection of a compound of the formula (IX):

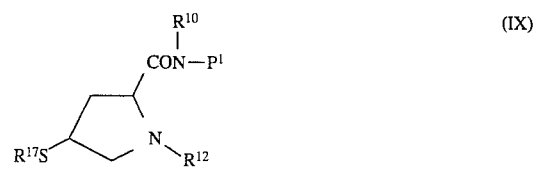

wherein $p^1$, $R^{10}$ and $R^{12}$ are as hereinbefore defined, optional substituents on $p^1$ are as hereinbefore defined and $R^{17}$ is a protecting group, for example $C_{1-6}$alkanoyl, $C_{1-6}$alkoxycarbonyl or benzoyl. Preferred values for $R^{17}$ are acetyl and t-butoxycarbonyl. The compounds of the formula (IX) can be converted to the compounds of the formula (VII) by standard methods of deprotection, for example acetyl groups can be removed by basic hydrolysis in aqueous alkanol, alkenol for example allyl alcohol, or tetrahydrofuran.

The compounds of the formula (IX) are novel and form another aspect of the present invention.

The compounds of the formula (IX) may be prepared by the reaction of an activated derivative of a compound of the formula (X), which may be formed in situ, with a compound of the formula (XI):

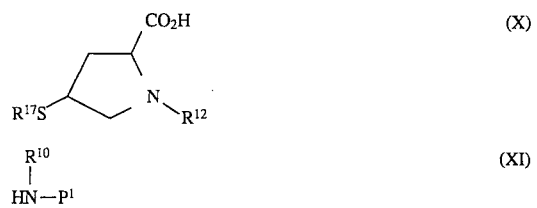

wherein $p^1$, $R^{10}$, $R^{12}$ and $R^{17}$ are as hereinbefore defined and optional substituents on $p^1$ are as hereinbefore defined. Activated derivatives of the compound of the formula (X) include acid halides, anhydrides and 'activated' esters such as 1H-benzol-1,2,3-triazol-1-yl, pentafluorophenyl and 2,4,5-trichlorophenyl esters or the benzimidazol-2-yl ester of the thiocarboxylic acid corresponding to (X). The reaction of the compounds of the formulae (X) and (XI) is performed under standard methods, for example, in the presence of sulfonyl chloride at ambient temperature.

The compounds of the formulae (X) and (XI) are prepared by standard methods known to the skilled chemist such as the methods of the Examples hereinafter, the methods described in EP-A-126587 or by methods analogous or similar thereto.

Suitably, in the compounds of the formula (VIII), $R^{14}$, $R^{15}$ and $R^{16}$ are independently selected from $C_{1-6}$ alkoxy such as methoxy, ethoxy, isopropoxy, n-propoxy or n-butoxy; aryloxy such as optionally substituted phenoxy; di-$C_{1-6}$alkylamino such as dimethylamino or diethylamino; diarylamino such as diphenylamino or any two of $R^{14}$–$R^{16}$ represent o-phenylenedioxy. Preferably each of $R^{14}$–$R^{16}$ have the same value and are $C_{1-6}$alkoxy for example methoxy, ethoxy, isopropoxy or n-butoxy or are phenoxy.

The compounds of the formula (VIII) are cyclized under conventional conditions known in the art to form compounds of the formula (V). Typical conditions are heating in a substantially inert organic solvent such as toluene, xylene or ethyl acetate at temperatures in the region 60°–150° C. Typically the reaction is performed in an atmosphere of nitrogen and is carried out in the presence of a radical scavenger for example hydroquinone.

The compounds of the formula (VIII) may be formed and cyclized in situ. The compounds of the formula (VIII) may conveniently be prepared by reacting compounds of the formulae (XII) and (XIII):

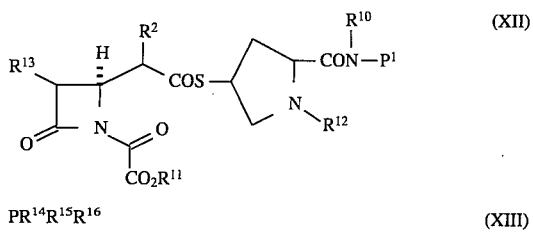

wherein $P^1$, $R^2$, $R^{10}$–$R^{16}$ are as hereinbefore defined and optional substituents on $P^1$ are as hereinbefore defined. Suitably the compound of the formula (XIII) is a phosphite or is the functional equivalent of such a compound.

The reaction between the compounds of the formulae (XII) and (XIII) is conveniently performed in an organic solvent such as toluene, xylene, ethyl acetate, chloroform, dichloromethane, acetonitrile or dimethylformamide. Typically the reaction is carried out at an elevated temperature for example 60°–150° C.

The compounds of the formula (XII) may be prepared by a number of methods known in the art. For example the compounds of the formula (XII) may be prepared by the acylation of a compound of the formula (XIV):

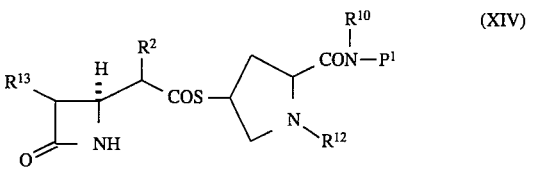

wherein $P^1$, $R^2$, $R^{10}$, $R^{12}$ and $R^{13}$ are as hereinbefore defined and optional substituents on $P^1$ are as hereinbefore defined with a compound of the formula (XV):

wherein $R^{11}$ is as hereinbefore defined.

The compounds of the formula (XIV) may be prepared by reacting compounds of the formulae (XVI) and (VII):

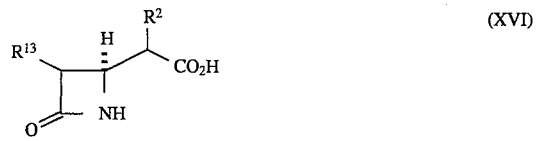

wherein $R^2$ and $R^{13}$ are as hereinbefore defined. The compounds of the formula (XVI) are known in the art and may be reacted with the compounds of the formula (VII) under conventional acylation methods known in the art.

Compounds of the formulae (VII), (XII) and (XIV) are novel and, as such, form another aspect of this invention.

The following biological test methods, data and Examples serve to illustrate the present invention.

Antibacterial Activity

The pharmaceutically acceptable carbapenem compounds of the present invention are useful antibacterial agents having a broad spectrum of activity in vitro against standard laboratory microorganisms, both Gram-negative and Gram-positive, which are used to screen for activity against pathogenic bacteria. The antibacterial spectrum and potency of a particular compound may be determined in a standard test system. In particular the carbapenems of the present invention show good stability to beta-lactamases and have a particularly good elimination half life in mammals. In general compounds show significant improvement over imipenem.

The antibacterial properties of the compounds of the invention may also be demonstrated in vivo in conventional tests.

Carbapenem compounds have generally been found to be relatively non-toxic to warm-blooded animals, and this generalisation holds true for the compounds of the present invention. Compounds representative of the present invention were administered to mice at doses in excess of those required to afford protection against bacterial infections, and no overt toxic symptoms or side effects attributable to the administered compounds were noted.

The following results were obtained for representative compounds on a standard in vitro test system using Diagnostic Sensitivity Test. The antibacterial activity is described in terms of the minimum inhibitory concentration (MIC) determined by the agar-dilution technique with an inoculum size of $10^4$ CFU/spot.

| ORGANISM | MIC (µg/ml) EXAMPLE 1 |
| --- | --- |
| S. aureus Oxford | 0.125 |
| E. coli DCO | 0.015 |
| P. morganii I + 001 | 0.015 |
| Enterobacter cloacae P99- | 0.008 |
| B. fragilis AMP S | 0.25 |

In the following examples, which are representative of the scope:

(a) NMR spectra were taken at 200 MHz or 400 MHz unless otherwise stated;

(b) Allyloxy means the propen-1-yloxy group —OCH$_2$CH=CH$_2$;

(c) THF means tetrahydrofuran;

(d) DMF means dimethylformamide;

(e) DMSO means dimethylsulphoxide;

(f) Evaporation of solvents was carried out under reduced pressure;

(g) HPLC means high pressure liquid chromatography;

(h) Temperatures are in degrees centigrade.

(i) TFA means trifluoroacetic acid; and (j) tlc means thin layer chromatography.

EXAMPLE 1

(1R,5S,6S,8R,2'S,4'S)-2-(2-(3-Sulfophenylcarbamoyl)pyrrolidin-4-ylthio)-6-(1-hydroxyethyl)-1-methylcarbapenem-3-carboxylic acid (dipotassium salt).

A solution of 4-nitrobenzyl (1R,5S,6S,8R,2'S,4'S)-2-(1-(4-nitrobenzyloxycarbonyl)-2-(2-(3-sulfophenylcarbamoyl)pyrrolidin-4-ylthio)-6-(1-hydroxyethyl)-1-methylcarbapenem-3-carboxylate diisopropylethylamine salt (720 mg, 0.87 mmol) in a mixture of ethyl acetate, ethanol, water (30 ml, 5 ml, 25 ml) and potassium bicarbonate (174.5 mg, 1.74 mmol) was hydrogenated at atmospheric pressure over palladium/carbon (10%) (500 mg) for 1 hour. The catalyst was filtered off, and the filtrate concentrated and purified by preparative HPLC (Nucleosil C-18), using water as the eluant. Concentration and lyophilisation of the required fractions gave the title compound (340 mg, 76%).

NMR (DMSO-$d_6$+AcOD-$d_4$): $\delta$1.17 (2d, 6H); 1.75 (m, 1H); 2.7 (m, 1H); 2.9 (m, 1H); 3.22 (dd, 1H); 3.45 (m, 2H); 3.77 (m, 1H); 3.96 (m, 2H); 4.18 (dd, 1H); 7.3 (m, 2H); 7.65 (m, 1H); 7.9 (s, 1H).

(2S,4S)-1-(4-Nitrobenzyloxycarbonyl)-2-(3-sulfophenylcarbamoyl)pyrrolidin-4-ylthioacetate (diisopropylethylamine salt).

(2S,4S)-1-(4-Nitrobenzyloxycarbonyl)-4-acetylthio-2-carboxypyrrolidine (1.5 g, 4 mmol) was treated with thionyl chloride (12 ml) at ambient temperature. The mixture was stirred at ambient temperature for 5 hours, the thionyl chloride evaporated and the residue dissolved in dichloromethane/toluene (1:1). The solvent was evaporated and the residual oil dried under vacuum for 1 hour and dissolved in dry dichloromethane (10 ml). This was added to a solution of 3-aminobenzenesulfonic acid (706 mg, 4 mmol) and diisopropylethylamine (1.42 ml, 8 mmol) in anhydrous DMF (10 ml) at 0°. The mixture was stirred at ambient temperature for 12 hours, the dichloromethane evaporated, and the residual DMF solution subjected to chromatography on a HP20SS column. The title compound was eluted with methanol(water+1% acetic acid), (gradient of methanol) (1.68 g, 79%).

NMR (DMSO-$d_6$+AcOD-$d_4$, 100° C.): $\delta$1.4 (m, 15H); 2.05 (m, 1H); 2.35 (s, 3H); 2.8 (m, 1H); 3.15 (q, 2H); 3.4 (m, 1H); 3.65 (m, 2H); 3.9–4.25 (m, 2H); 4.5 (dd, 1H); 5.25 (s, 2H); 7.1–7.75 (m, 5H); 7.9 (m, 1H); 8.1 (d, 2H).

4-Nitrobenzyl (1R,5R,6S,8R)-6-(1-hydroxyethyl)-1-methyl-2-diphenylphosphoryloxycarbapenem-3-carboxylate was prepared as follows: To a solution of 4-nitrobenzyl (1R,5R,6S,8R)-6-(1-hydroxyethyl)-1-methyl-2-oxocarbapenem-3-carboxylate [prepared in situ from 4-nitrobenzyl 2-diazo-3-oxo-4-(R)-methyl-4-[3S,4R)-3-(1-(R)-hydroxyethyl)-2-oxoazetidin-4-yl]-butanoate and rhodium octanoate: see for example EP-A-208889] and di-isopropylethylamine (1.1 equivalents) in acetonitrile, at 0° C., under an argon atmosphere, was added dropwise diphenyl chlorophosphate (1.1 equivalents). The solution was stirred at ambient temperature for 30 minutes to form the corresponding 2-diphenylphosphoryloxycarbapenem.

4-Nitrobenzyl (1R,5S,6S,8R,2'S,4',S)-2-(1-(4-nitrobenzyloxycarbonyl-2-(3-sulfophenylcarbamoyl)pyrrolidin-4-ylthio)-6-(1-hydroxyethyl)-1-methylcarbapenem-3-carboxylate (diisopropylethylamine salt).

(2S,4S)-1-(4-Nitrobenzyloxycarbonyl)-2-(3-sulfophenylcarbamoyl)pyrrolidin-4-ylthioacetate diisopropylethylamine salt (0.8 g, 1.53 mmol) in methanol (40 ml) was treated with 1M NaOH (3.83 ml, 2.5 mmol) at ambient temperature for 1 hour. The mixture was then acidified to pH3 at 0° with 6M HCl, evaporated and dried under vacuum for 1 hour. The crude thiol was dissolved in DMF (5 ml) and added to a solution of 4-nitrobenzyl (1R,5R,6S,8R)-6-(1-hydroxyethyl)-1-methyl-2- diphenylphosphoryloxycarbapenem-3-carboxylate (890 mg, 1.5 mmol) in DMF (10 ml), diisopropylethylamine (520 μl, 3 mmol), tri-n-butylphosphine (373 μl 1.5 mmol) and water (27 μl 1.5 mmol) at 0° and left overnight. The crude reaction mixture was subjected to chromatography on a HP20SS column using acetonitrile/water as eluant (gradient acetonitrile) to give the title compound (728 mg, 59%).

NMR (DMSO-$d_6$+AcOD-$d_4$): $\delta$1.3 (m, 21H); 1.9 (m, 1H); 2.85 (m, 1H); 3.15 (q, 2H); 3.3 (dd, 1H); 3.4 (m, 1H); 3.65 (m, 3H); 3.8–4.1 (m, 2H); 4.15 (m, 1H); 4.25 (dd, 1H); 4.5 (m, 1H); 5.28–5.5 (m, 4H); 7.2–8.3(m, 12H).

EXAMPLE 2

(1R,5S,6S,8R,2'S,4'S)-2-(2-(2-Hydroxy-5-sulfophenylcarbamoyl)pyrrolidin-4-ylthio)-6-(1-hydroxyethyl)-1-methylcarbapenem-3-carboxylic acid (dipotassium salt).

The title compound was prepared from 4-nitrobenzyl (1R,5R, 6S,8R,2'S,4'S)-2-(1-(4-nitrobenzyloxycarbonyl)-2-(2-hydroxy-5-sulfophenylcarbapenem-3-carboxylate diisopropylethylamine salt, using a similar method to that of example 1, except the solvent used in the hydrogenation was water.

NMR (DMSO-$d_6$+AcOD-$d_4$): $\delta$1.15 (2d, 6H); 1.75 (m, 1H); 2.65 (m, 2H); 3.2 (dd, 1H); 3.4 (m, 1H); 3.51 (m, 1H); 3.63 (m, 1H); 3.94 (m, 1H); 4.02 (m, 1H); 4.18 (dd, 1H); 6.82 (dd, 1H); 7.22 (dd, 1H); 8.42 (s, 1H).

(2S,4S)-1-(4-Nitrobenzyloxycarbonyl)-2-(2-hydroxy-5-sulfophenylcarbamoyl)pyrrolidin-4-ylthioacetate (diisopropylethylamine salt).

The title compound was prepared from 3-amino-4-hydroxybenzenesulfonic acid using a similar method to that of example 1.

NMR (DMSO-$d_6$+TFA-d, 70° C.): 1.35 (m, 15H); 2.1 (m, 1H); 2.3 (s, 3H); 2.8 (m, 1H); 3.15 (q, 2H); 3.4 (m, 1H); 3.65 (m, 2H); 3.9–4.25 (m, 2H); 4.65 (dd, 1H); 5.25 (s, 2H); 6.85 (d, 1H); 7.3 (dd, 1H); 7.6 (d, 2H); 8.1 (d, 2H); 8.2 (d, 1H).

4-Nitrobenzyl (1R,5R,6S,8R,2'S,4'S)-2-(1-(4-nitrobenzyloxycarbonyl)-2-(2-hydroxy-5-sulfophenylcarbamoyl)pyrrolidin-4-ylthio)-6-(1-hydroxyethyl)-1-methylcarbapenem-3-carboxylate (diisopropylethylamine salt).

The title compound was prepared from (2S,4S)-1-(4-nitrobenzyloxycarbonyl)-2-(2-hydroxy-5-sulfophenylcarbamoyl)pyrrolidin-4-ylthioacetate diisopropylethylamine salt using a similar method to that of example 1.

NMR (DMSO-$d_6$+AcOD-$d_4$): $\delta$1.2 (m, 21H); 2.05 (m, 1H); 2.85 (m, 1H); 3.1 (q, 2H); 3.28 (dd, 1H); 3.4 (m, 1H); 3.6 (m, 3H); 3.8–4.2 (m, 3H); 4.25 (dd, 1H); 4.6 (m, 1H); 5.1–5.4 (m, 4H); 7.05–7.25 (m, 2H); 7.25–7.45 (m, 1H); 7.45–7.7 (m, 3H); 8.0–8.3(m, 5H).

EXAMPLE 3

(1R,5S,6R,8R,2'S,4'S)-2-(2-(2-Methoxy-5-methyl-4-sulfophenylcarbamoyl)pyrrolidin-4-ylthio)-6-(1-hydroxyethyl)-1-methylcarbapenem-3-carboxylic acid (dipotassium salt).

The title compound was prepared from 4-nitrobenzyl (1R,5R,6S,8R,2'S,4'S)-2-(1-(4-nitrobenzyloxycarbonyl)-2-(2-methoxy-5-methyl-4-sulfophenylcarbamoyl)pyrrolidin-4-ylthio)-6-(1-hydroxyethyl)-1-methylcarbapenem-3-carboxylate diisopropylethylamine salt using a similar method to that of Example 2.

NMR (DMSO-$d_6$+AcOD-$d_4$): δ1.18 (2d, 6H); 1.78 (m, 1H); 2.48 (s, 3H); 2.6–2.8 (m, 2H); 3.2 (dd, 1H); 3.42 (m, 1H); 3.51 (m, 1H); 3.65 (m, 1H); 3.82 (s, 3H); 3.9–4.1 (m, 2H); 4.15 (dd, 1H); 7.44 (s, 1H); 8.05 (s, 1H).

(2S,4S)-1-(4-Nitrobenzyloxycarbonyl)-2-(2-methoxy-5-methyl-4-sulfophenylcarbamoyl)pyrrolidin-4-ylthioacetate (diisopropylethylamine salt).

The title compound was prepared from 4-amino-5-methoxy-2-methylbenzenesulfonic acid using a similar method to that of Example 1.

NMR (DMSO-$d_6$+TFA-d): δ1.35 (m, 15H); 2.1 (m, 1H); 2.3 (s, 3H); 2.45 (s, 3H); 2.8 (m, 1H); 3.15 (q, 2H); 3.4 (m, 1H); 3.65 (m, 2H); 3.9–4.25 (m, 2H); 4.7 (dd, 1H); 5.25 (s, 2H); 7.45 (s, 1H); 7.65 (d, 2H); 7.85 (m, 1H); 8.2 (d, 2H).

4-Nitrobenzyl (1R,5R,6S,R,8R,2'S,4'S)-2-(1-(4-nitrobenzyloxycarbonyl)-2-(2-methoxy-5-methyl-4-sulfophenylcarbamoyl)pyrrolidin-4-ylthio)-6-(1-hydroxyethyl)-1-methylcarbapenem-3-carboxylate (diisopropylethylamine salt).

The title compound was prepared from the product of the previous step using a similar method to that of example 1.

NMR (DMSO-$d_6$+AcOD-$d_4$): δ1.25 (m, 21H); 2.05 (m, 1H); 2.45 (s, 3H); 2.85 (m, 1H); 3.15 (q, 2H); 3.3 (dd, 1H); 3.4 (m, 1H); 3.55 (m, 1H); 3.65 (m, 2H); 3.75 (s, 3H); 3.8–4.2 (m, 3H); 4.25 (dd, 1H); 4.6 (m, 1H); 5.2–5.4 (m, 4H); 7.47 (s, 1H); 7.5–7.8 (m, 5H); 8.1–8.25 (m, 4H).

EXAMPLE 4

(1R,5S,6S,8R,2'S,4'S)-2-(2-(2-Sulfophenylcarbamoyl)pyrrolidin-4-ylthio)-6-(1-hydroxyethyl)-1-methylcarbapenem-3-carboxylic acid (dipotassium salt).

The title compound was prepared from 4-nitrobenzyl (1R,5R, 6S,8R,2'S,4'S)-2-(1-(4-nitrobenzyloxycarbonyl)-2-(2-sulfophenylcarbamoyl)pyrrolidin-4-ylthio)-6-(1-hydroxyethyl)-1-methylcarbapenem-3-carboxylate diisopropylethylamine salt using a similar method to that of example 1, except the solvent used in the hydrogenation was water/ethyl acetate (3:1).

NMR (DMSO-$d_6$+AcOD-$d_4$): δ1.15 (2d, 6H); 1.7 (m, 1H); 2.7 (m, 2H); 3.2 (dq, 1H); 3.3–3.6 (m, 3H); 3.95 (m, 2H); 4.2 (dd, 1H); 7.05 (t, 1H); 7.3 (t, 1H); 7.7 (d, 1H); 8.3 (d, 1H).

(2S,4S)-1-(4-Nitrobenzyloxycarbonyl)-2-(2-sulfophenylcarbamoyl)pyrrolidin-4-ylthioacetate (diisopropylethylamine salt).

The title compound was prepared from 2-aminobenzenesulfonic acid using a similar method to that of example 1.

NMR (DMSO-$d_6$+TFA-d): δ1.3 (m, 15H); 2.3 (s, 3H); 2.5–2.8 (m, 2H); 3.15 (q, 2H); 3.4–3.75 (m, 3H); 4.0–4.25 (m, 2H); 4.3–4.5 (t, 1H); 5.2 (s, 2H); 6.9–8.3 (m, 8H).

4-Nitrobenzyl (1R,5R,6S,8R,2'S,4'S)-2-(1-(4-nitrobenzyloxycarbonyl)-2-(2-sulfophenylcarbamoyl)pyrrolidin-4-ylthio)-6-(1-hydroxyethyl)-1-methylcarbapenem-3-carboxylate (diisopropylethylamine salt).

The title compound was prepared from the product of the previous step using a similar method to that of example 1.

NMR (DMSO-$d_6$+AcOD-$d_4$): δ0.9–1.0 (m, 21H), 2.0 (m, 1H); 2.85 (m, 1H); 3.15 (q, 2H); 3.3 (dd, 1H); 3.5–3.7 (m, 4H); 3.9–4.1 (m, 2H); 4.15–4.5 (m, 4H); 5.1–5.5 (m, 4H); 7.05 (t, 1H); 7.25 (m, 1H); 7.55 (d, 1H); 7.65–7.8 (m 4H); 8.0 (d, 1H); 8.2–8.45 (m, 3H).

EXAMPLE 5

(1R,5S,6S,8R,2'S,4'S)-2-(2-(2-Hydroxy-4-sulfo-1-naphthylcarbamoyl)-pyrrolidin-4-ylthio)-6-(1-hydroxyethyl)-1-methylcarbapenem-3-carboxylic acid (dipotassium salt).

The title compound was prepared from 4-nitrobenzyl (1R,5R,6S, 8R,2'S,4'S)-2-(1-(4-nitrobenzyloxycarbonyl)-2-(2-hydroxy-4-sulfo-1-naphthylcarbamoyl)pyrrolidin-4-ylthio)-6-(1-hydroxyethyl)-1-methylcarbapenem-3-carboxylate diisopropylethylamine salt using a similar method to that of example 1.

NMR: (DMSO-$d_6$+AcOD-$d_4$): δ1.1 (2d, 6H); 1.95 (m, 1H); 2.85 (m, 1H); 2.95 (m, 1H); 2.99 (m, 1H); 3.2 (dd, 1H); 3.4 (m, 1H); 3.6 (m, 1H); 3.8 (m, 1H); 3.98 (m, 1H); 4.18 (dd, 1H); 4.28 (t, 1H); 4.7 (m, 1H); 5.3 (s, 2H); 7.32 (dd, 1H); 7.45 (dd, 1H); 7.68 (d, 1H); 7.78 (s, 1H); 8.73 (d, 1H).

(2S,4S)-1-(4-Nitrobenzyloxycarbonyl)-2-(2-hydroxy-4-sulfo-1-naphthylcarbamoyl)pyrrolidin-4-ylthioacetate (diisopropylethylamine salt).

The title compound was prepared from 1-amino-2-hydroxynaphthylenesulfonic acid using a similar method to that of example 1.

NMR (DMSO-$d_6$+AcOD-$d_4$): δ1.35 (m, 15H); 2.15 (m, 1H); 2.3 (s, 3H); 2.8 (m, 1H); 3.15 (q, 2H); 3.35 (m, 1H); 3.6 (m, 2H); 3.9–4.25 (m, 2H); 7.0–7.5 (m, 2H); 7.5–8.0 (m, 4H); 8.15 (d, 2H); 8.75 (m, 1H).

4-Nitrobenzyl (1R,5R,6S,8R,2'S2'S)-2-(1-(4-nitrobenzyloxycarbonyl)-2-(2-hydroxy-4-sulfo-1-naphthylcarbamoyl)pyrrolidin-4-ylthio)-6-(1-hydroxyethyl)-1-methylcarbapenem-3-carboxylate (diisopropylethylamine salt).

The title compound was prepared from the product of the previous step using a similar method to that of example 1.

NMR: (DMSO-$d_6$+AcOD-$d_4$): δ1.09 (d, 3H); 1.11 (d, 3H); 2.1 (m, 1H); 2.94 (m, 1H); 3.1–3.5 (m, 2H); 3.6 (m, 1H); 3.9–4.1 (m, 2H); 4.15–4.35 (m, 2H); 4.7 (m, 1H); 5.15–5.55 (m, 4H); 7.1–7.3 (m, 2H); 7.3–7.5 (m, 6H); 8.0–8.3 (m, 4H); 8.7 (d, 1H).

EXAMPLE 6

(1R,5S,6S,8R,2'S,4'S)-2-(2-(3-Methylsulfonylcarbamoylphenylcarbamoyl)pyrrolidin-4-ylthio)-6-(1-hydroxyethyl)-1-methylcarbapenem-3-carboxylic acid.

To a solution of 4-nitrobenzyl (1R,5S,6S,8R,2'S,4'S)-2(2-(3-methylsulfonylcarbamoylphenylcarbamoyl)-1-(4-nitrobenzyloxycarbonyl)pyrrolidin-4-ylthio)-6-(1-hydroxyethyl)-1-methylcarbapenem-3-carboxylate (360 mg, 0,416 mM) in THF (freshly distilled from CaH$_2$; 35 ml) was added a suspension of 10% palladium on charcoal (150 mg) in water (15 ml) containing sodium hydrogen carbonate (35 mg, 0,416 mM). The resulting suspension was stirred in an atmosphere of hydrogen for 2 hours. The catalyst was removed by filtration through a millipore 0.2 μm syringe filter and the filtrate partitioned between ethyl acetate and water (50 ml of each). The ethyl acetate layer was extracted with more water and the combined aqueous extracts washed with ether and partially evaporated (high vacuum & 'Drikold' condenser). The concentrated aqueous layer (approximately 30 ml) was freeze-dried overnight to give the crude title compound (350 mg).

Sodium hydrogen carbonate (150 mg) was added to the solution of crude material before being purified by column chromatography using a column of Diaion HP2055 resin (300×30 mm), eluting with water. Fractions containing the required product were combined and evaporated partially to dryness (as above) and then freeze dried overnight to give the title compound (100 mg).

NMR: 1.32 (d, 6H); 2.13 (m, 1H); 3.08 (m, 1H); 3.37 (dd, 1H); 3.40 (s, 3H); 3.54 (dd, 1H); 3.90 (dd, 1H); 4.13 (m, 2H); 4.37 (dd, 1H); 4.57 (t, 1H); 7.59(t, 1H); 7.86(d, 1H); 7.98(d, 1H); 8.34(s, 1H); MS: M+552.

The starting material was prepared as follows:
3-Amino-N-methylsulfonylbenzamide A solution of 3-nitro-N-methylsulfonylbenzamide (R.N. [33920-36-4]; Ger Offen. DE 2002065—July 1971; 2.4 g, 10 mM) in acetic acid (100 ml) containing 10% palladium on charcoal (0.3 g) was stirred under an atmosphere of hydrogen at ambient temperature and atmospheric pressure, for 2 hours. The hydrogen uptake was 800 ml. The suspension was filtered through Whatman No 50 filter paper and the filtrate evaporated. The resulting oil was dissolved in absolute ethanol (200 ml) and acidified with concentrated hydrochloric acid. A solid began to crystallise out. The solution was cooled to 5° C. for 2 hours and the solid collected and washed with cold ethanol. 3-Amino-N-methylsulfonylbenzamide hydrochloride was obtained as pale pink crystals (10.5 g; m.p. 224.5°–228° C.).

NMR (DMSO-$d_6$): δ3.38 (s, 3H); 7.53 (m, 2H); 7.8 (m, 2H); 7.9–10.8 (broad, 3H).

(2S,4S)-4-Acetylthio-1-(4-nitrobenzyloxycarbonyl)-2-(3-methylsulfonylcarbamoylphenylcarbamoyl)pyrrolidine.

Diisopropylethylamine (2.8 ml, 20 mM) followed by chlorotrimethylsilane (1.3 ml, 10 mM) was added to a stirred solution of 3-amino-N-methylsulfonylbenzamide hydrochloride (2.5 g, 10 mM) in THF (distilled from CaH$_2$; 30 ml) under an argon atmosphere. The solution was allowed to stand for 30 minutes and a crystalline solid separated.

Meanwhile, 4-acetylthio-1-(4-nitrobenzyloxycarbonyl)-2-carboxypyrrolidine (1.84 g, 5 mM) dissolved in THF (30 ml) was treated with N-methylmorpholine (1.1 ml, 10 mM). This solution was cooled to −15° C. with stirring under an argon atmosphere, and treated with isobutyl chloroformate (0.66 ml, 5 mM) in one portion.

After 5 minutes, this solution was treated with the supernatant liquor from the trimethylsilyl derivative of the aniline (prepared above) at such a rate as to maintain the temperature below 0° C. When the addition was complete, the mixture was stirred for 15 minutes and the solvent evaporated. The residue was partitioned between ethyl acetate (200 ml) and 1M aqueous hydrochloric acid (100 ml). A solid crystallised out of the mixture which was collected and washed with ethyl acetate and water and then air-dried to give (2S,4S)-4-acetylthio-1-(4-nitrobenzyloxycarbonyl)-2-(3-methylsulfonylcarbamoylphenylcarbamoyl)pyrrolidine as a white crystalline solid, (2.0 g; m.p. 240.5°–242° C.).

NMR (DMSO-$d_6$): 1.93 (m, 1H); 2.33 (s, 3H); 2.80 (m, 1H); 3.33 (s, 3H); 4.05 (m, 2H); 4.48 (m, 1H); 5.18 (q, 2H); 7.48 (m, 2H); 7.64 (m, 2H); 7.82 (m, 2H); 7.95 (d, 1H); 8.15 (d, 1H); 8.24 (d, 1H); 10.3 (s, 1H); 12.15 ( s, 1H).

4-Nitrobenzyl (1R,5S,6S,8R,2'S,4'S)-2-(2-(3-methylsulfonylcarbamoylphenylcarbamoyl)-1-(4-nitrobenzyloxycarbonyl)pyrrolidin-4-ylthio)-6-(1-hydroxyethyl)-1-methylcarbapenem-3-carboxylate To a solution of (2S,4S)-4-acetylthio-1-(4-nitrobenzyloxycarbonyl-2-(3-methylsulfonylcarbamoylphenylcarbamoyl)pyrrolidine (0.9 g, 1.6 mM) in absolute ethanol (8 ml) was added methylamine (33% solution in ethanol, 2 ml, 16 mM) and the mixture stirred under argon for 20 minutes. The solution was partitioned between ethyl acetate (70 ml) and hydrochloric acid (1M; 50 ml) and the ethyl acetate layer separated and washed with water (50 ml), saturated brine (50 ml), dried over magnesium sulphate and evaporated.

The resulting thiol was dissolved in acetonitrile (20 ml) and the solution treated with diisopropylethylamine (1.0 ml, 5.6 mM). To this solution was added 4-nitrobenzyl (1R,5R,6S,8R)-6-(1-hydroxyethyl)-1-methyl-2-diphenylphosphoryloxycarbapenem-3-carboxylate (1.0 g, 1.68 mM) and the mixture stirred until complete solution was obtained. The mixture was allowed to stand for 16 hours at 5° C. The solvent was evaporated and the residue partitioned between ethyl acetate (100 ml) and hydrochloric acid (1M; 50 ml). The ethyl acetate layer was separated and washed with hydrochloric acid (1M; 50 ml), water (50 ml), saturated brine (50 ml), dried over magnesium sulphate and evaporated. The residue was chromatographed on silica gel (Merck 9385, column 40 mm diameter filled to a depth of 120 mm), eluting with a gradient of dichloromethane; methanol (95:5) to (1:1). Fractions containing the required product were combined and evaporated. The title compound was obtained as a pale yellow foam (0.45 g).

NMR (CDCl$_3$-DMSO-$d_6$): 1.29 (t, 6H), 2.10 (m, 1H), 3.23 (q, 1H); 3.37 (s, 3H); 3.45 (m, 3H); 3.76 (m, 1H); 4.10 (t, 2H); 4.29 (q, 1H); 4.54 (t, 1H);

EXAMPLE 7

(1R,5S,6S,8R,2'S,4'S)-2-(2-(3-(1H-Tetrazol-5-yl)phenylcarbamoyl)pyrrolidin-5-ylthio)-6-(1-hydroxyethyl)-1-methylcarbapenem-3-carboxylic acid.

To a solution of 4-nitrobenzyl (1R,5S,6S,8R,2'S,4'S)-2-(2-(3-1H-tetrazol-5-yl)phenylcarbamoyl)-1-(4-nitrobenzyloxycarbonyl)pyrrolidin-4-ylthio)-6-(1-hydroxyethyl)-1-methylcarbapenem-3-carboxylate(750 mg) in THF (20 ml) was added a solution of sodium hydrogen carbonate (80 mg, 0.95 mmol) in water (20 ml). 10% Palladium on charcoal (200 mg) was added and the mixture hydrogenated under an atmosphere of hydrogen for 1 hour. The palladium catalyst was filtered and a further 200 mg of catalyst added to the filtrate, which was hydrogenated in an atmosphere of hydrogen for 3 hours. The catalyst was again filtered, the filtrate extracted with ethyl acetate (25 ml) and ether (20 ml) and the aqueous layer freeze-dried to give a brown solid (240 mg). The solid was dissolved in water (40 ml) with sodium hydrogen carbonate (120 mg) and purified by chromatography on DIAION HP20SS resin (110 ml), eluting with water. The solvent was reduced, by evaporation, to 20 ml then freeze-dried to give the title product (130 mg).

NMR (DMSO-$d_6$): 1.8 (d, 6H); 2.56–2.62 (m, 1H); 3.43–3.58 (m, 1H); 3.79–3.9 (m, 2H); 3.93–4.06 (m, 1H); 4.30–4.40 (dd, 1H); 4.51–4.70 (m, 2H); 4.78–4.87 (dd, 1H); 4.98–5.07 (t, 1H); 8.07–8.16 (t, 1H); 8.3 (fine split dd, 1H); 8.42 (fine split dd, 1H); 8.98 (fine split s, 1H). MS: (M—H)$^-$ 498; 520 (for mono sodium salt): 542 (for di sodium salt).

The starting material was prepared as follows:
Vilsmeier reagent was prepared by treatment of DMF (0.72 ml, 9.25 mmol) in dichloromethane (40 ml) under argon with oxalylchloride (0.72 ml, 8.3 mmol) at −20° C. for 30 minutes (2S,4S)-4-Acetylthio-1-(4-nitrobenzyloxycarbonyl)-2-carboxypyrrolidine (3 g, 8.1 mmol) in dichloromethane (10 ml) was added, followed by N-methylmorpholine (1.1 ml, 10.1 mmol) and stirring continued at −20° C. for 45 minutes. Formation of the acid chloride was found to be incomplete so a further (0.4 ml, 4.6 mmol) oxalylchloride was added and the mixture stirred at −20° C. for 30 minutes. The solvent was removed to give a brown solid which was azeotroped with toluene. The solid was dissolved in dichloromethane (50 ml) and cooled to −20° C. under an atmosphere of argon. A mixture of 3-(1H-tetrazol-5-yl)aniline (1.5 g; 9.3 mmol) and N-methylmorpholine (2.5 ml, 22.9 mmol) in DMF (4 ml) was added and the mixture allowed to warm to ambient temperature over 20 hours. After dilution with dichloromethane (30 mls) the mixture was washed with aqueous 1N HCl solution and brine (50 ml), dried (MgSO$_4$) and the solvent removed by evaporation to give a brown gum. This was purified by flash chromatography on silica, eluting with a gradient of dichloromethane; glacial acetic acid (100:3) to dichloromethane: ethylacetate: glacial acetic acid (40:60:3) and azeotroped with toluene to give (2S,4S)-4-acetylthio-1-(4-nitrobenzyloxycarbonyl)-2-(3-(1H-tetrazol-5-yl)phenylcarbamoyl)pyrrolidine as a pale yellow solid (3 g).

NMR (DMSO-d$_6$): 1.83–2.05 (m, 1H); 2.35 (s, 3H); 2.71–2.92 (m, 1H); 3.91–4.19 (m, 2H); 4.40–4.58 (m, 1H); 5.01–5.35 (m, 2H); 7.45–7.59 (m, 2H); 7.61–7.79 (m, 3H); 7.9 (d, 1H); 8.24 (d, 1H); 8.39 (d, 1H); 10.34 (s, 1H). MS: $(M-H)^-=510$.

To a solution of (2S,4S)-4-acetylthio-1-(4982 -nitrobenzyloxycarbonyl)-2-(3-(1H-tetrazol-5-yl)phenylcarbamoyl)pyrrolidine (500 mg, 0.98 mmol) in ethanol (5 ml) at 5° C. under an atmosphere of argon, was added, a 33% solution of methylamine (1 ml, 8.4 mmol). The mixture was stirred at 5° C. for 10 minutes before being partitioned between ethyl acetate and dilute aqueous HCl solution. The organic layer was washed with brine, dried (MgSO$_4$) and the solvent removed to give a pale yellow foam. This product was used without further purification or identification.

4-Nitrobenzyl (1R,5R,6S,8R)-6-(1-hydroxyethyl)-1-methyl-2-trifluoromethanesulfonyloxycarbapenem-3-carboxylate was made using the method described in example 1 for the preparation of the corresponding 2-diphenylphosphoryloxy carbapenem, except that trifluoromethanesulfonicanhydride was used in place of diphenylchlorophosphate and 2 equivalents of diisopropylethylamine were used. The product was used without analysis.

To a solution of 4-nitrobenzyl (1R,5R,6S,8R)-6-(1-hydroxyethyl)-1-methyl-2-trifluoromethanesulfonyloxycarbapenem-3-carboxylate (490 mgs, 0.98 mmol) in acetonitrile (5 ml), at −40° C., was added a solution of 1-(4-nitrobenzyloxycarbonyl)-2-(3-(1H-tetrazol-5-yl)phenylcarbamoyl)pyrrolidin-4-ylthiol (from 500 mgs of its thioacetate) in acetonitrile (5 ml) and diisopropylethylamine (0.52 ml, 2.93 mmol). The mixture was stored at 5° C. for 20 hours, the solvent removed and the yellow gum redissolved in dichloromethane (30 ml) which was washed with 1N HCl (2×25 ml) and brine (25 ml). In the washing procedure yellow gum formed which redissolved in ethyl acetate. The two organic phases were dried (MgSO$_4$) and evaporated to give a pale yellow solid (760 mg) which was used without further purification.

EXAMPLE 8

(1R,5S,6S,8R,2'S,4'S)-2-(2-(1-Carboxy-3-naphthylcarbamoylpyrrolidin-4-ylthio)-6-(1-hydroxyethyl)-1-methylcarbapenem-3-carboxylic acid, (dipotassium salt).

A solution of (1R,5S,6S,8R,2'S,4'S)-2-(1-(4-nitrobenzyloxycarbonyl)-2-(1-carboxy-3-naphthylcarbamoyl)pyrrolidin-4-ylthio)-6-(1-hydroxyethyl)-1-methylcarbapenem-3-carboxylic acid dipotassium salt (440 mg, 0.56 mmol) in water (25 ml) was hydrogenated on palladium/carbon (10%, 200 mg) at atmospheric pressure. The reaction was followed by HPLC. After filtering off the catalyst and concentrating the solution, the residue was purified by preparative HPLC (Nucleosil C-18), eluting with water/acetonitrile, to give the title compound (142 mg, 42%).

NMR: (DMSO-d$_6$+AcOD-d$_4$) δ1.16 (m, 6H); 1.85 (m, 1H); 2.7 (m, 1H); 2.9 (m, 1H); 3.2 (dd, 1H); 3.4 (m, 1H); 3.47 (dq, 1H); 3.72 (m, 1H); 3.97 (dq, 1H); 4.05 (m, 1H); 4.16 (dd, 1H); 7.5 (m, 2H); 7.89 (m, 1H); 8.32 (m, 1H); 8.46 (m, 1H); 8.77 (m, 1H).

(2S,4S)-1-(4-Nitrobenzyloxycarbonyl)-2-(1-carboxy-3-naphthylcarbamoyl)pyrrolidin-4-ylthioacetate.

(2S,4S)-1-(4-Nitrobenzyloxycarbonyl)-4-acetylthio-2-carboxypyrrolidine (1.5 g, 4 mmol) was treated at ambient temperature with thionyl chloride (12 ml). The mixture was stirred for 5 hours, thionyl chloride evaporated and the residue dissolved in dichloromethane/toluene (1:1). The solvent was evaporated and the residual oil dried under vacuum for 1 hour and dissolved in dichloromethane (10 ml). This solution was added to a solution of 3-amino-1-naphthoic acid (762 mg, 4 mmol) and diisopropylethylamine (1.75 ml, 10 mmol) in dichloromethane (25 ml) at 0° C. and stirred for 12 hours at ambient temperature. The solvent was evaporated and the residue purified by subjecting to chromatography on a HP20SS column eluting with acetonitrile/(water+acetic acid 1%) using a gradient of acetonitrile to give the title compound (1.5 g, 68.5%).

NMR (DMSO-d$_6$), 100°): δ2.1 (m, 1H); 2.34 (s, 3H); 2.85 (m, 1H); 3.45 (m, 1H); 3.85–4.3 (m, 2H); 4.57 (dd, 1H); 5.23 (dd, 2H); 7.4–7.7 (m, 4H); 7.7–8.2 (m, 3H); 8.2–8.5 (m, 2H); 8.65–8.9 (m, 1H).

Allyl (1R,5R,6S,8R,2'S,4'S)-2-(1-(4-nitrobenzyloxycarbonyl)-2-(1-carboxy-3-naphthylcarbamoyl)pyrrolidin-4-ylthio)-6-(1-hydroxyethyl)-1-methylcarbapenem-3-carboxylate (diisopropylethylamine salt).

(2S,4S)-1-(4-Nitrobenzyloxycarbonyl)-2-(1-carboxy-3-naphthylcarbamoyl)pyrrolidin-4-ylthioacetate (537 g, 1 mmol) in methanol (25 ml) was treated with 1M NaOH (2.5 ml, 2.5 mmol) for 1 hour at ambient temperature. The reaction mixture was acidified to pH3 at 0° with 6M HCl, evaporated and dried under vacuum for 1 hour. The resulting crude thiol was dissolved in DMF (6 ml) and added to a solution of allyl (1R,5R,6S,8R)-6-(1-hydroxyethyl)-1-methyl-2-diphenylphosphoryloxycarbapenem-3-carboxylate (499 mg, 1 mmol) in DMF (6 ml), in the presence of diisopropylethylamine (350 μl, 2 mmol), tri-n-butylphosphine (250 g, 1 mmol) and water (18 μl, 1 mmol) at ambient temperature and left overnight. The product was purified by subjecting to chromatography on a HP20SS column using acetonitrile/water (gradient to acetonitrile) as eluant to give the title compound (540 mg, 72.5%).

NMR (DMSO-d$_6$): δ1.18 (m, 15H); 1.25 (m, 6H); 2.0 (m, 1H); 2.85 (m, 1H); 3.13 (q, 2H); 3.25 (dd, 1H); 3.4 (m, 1H); 3.6 (m, 3H); 3.97 (m, 2H); 4.1–4.3 (m, 2H); 4.4–4.75 (m, 3H); 5.0–5.4 (m, 4H); 5.87 (m, 1H); 7.4–7.6 (m, 3H); 7.67 (d, 1H); 7.8–7.95 (m, 2H); 8.2–8.4 (m, 2H); 8.55 (m, 1H); 8.8 (m, 1H).

(1R,5S,6S,8R,2'S,4'S)-2-(1-(4-Nitrobenzyloxycarbonyl)-2-(1-carboxy-3-naphthylcarbamoyl)pyrrolidin-4-ylthio)-6-(1-hydroxyethyl)-1-methyl carbapenem-3-carboxylic acid (dipotassium salt).

A solution of allyl (1R,5S,6S,8R,2'S,4'S)-2-(1-(4-nitrobenzyloxycarbonyl)-2-(1-carboxy-3-naphthylcarbamoyl)pyrrolidin-4-ylthio)-6-(1-hydroxyethyl)-1-methylcarbapenem-3-carboxylate diisopropylethylamine salt (540 mg, 0.726 mmol) in anhydrous THF (30 ml) was treated with triphenylphosphine (19 mg, 0.072 mmol) potassium hexanoate (0.46M in ethyl acetate), (3.5 ml, 1.6 mmol) and tetrakis(triphenylphosphine)palladium (2.5 mg, 0.02 mmol) at ambient temperature for 1 hour. The mixture was diluted with ethyl acetate (30 ml), the precipitate filtered off and the filtrate washed with ethyl acetate and dried to give the title compound (440 mg, 78%).

NMR (DMSO-d$_6$): δ1.1–1.3 (m, 6H); 1.95 (m, 1H); 2.85 (m, 1H); 3.2 (dd, 1H); 3.3–3.5 (m, 2H); 3.7 (m, 1H); 3.8–4.2

(m, 3H); 4.55 (m, 1H); 5.2 (dd, 1H); 5.3 (s, 1H); 7.5 (m, 3H); 7.67 (d, 1H); 7.9 (d, 2H); 8.25 (m, 2H); 8.5 (m, 1H); 8.8 (m, 1H).

EXAMPLE 9

(1R,5S,6S,8R,2'S,4'S)-2-(2-(2-carboxy-3-naphthylcarbamoyl)pyrrolidin-4-ylthio)-6-(1-hydroxyethyl)-1-methylcarbapenem-3-carboxylic acid.

The title compound was prepared from (1R,5S,6S,8R,2'S, 4'S)-2-(1-(4-nitrobenzyloxycarbonyl)-2-(2-carboxy-3-naphthylcarbamoyl)pyrrolidin-4-ylthio)-6-(1-hydroxyethyl)-1-methylcarbapenem-3-carboxylic acid dipotassium salt using the method of example 8.

NMR (DMSO-$d_6$+AcOD-$d_4$): δ1.15 (m, 6H); 1.85 (m, 1H); 2.7–2.9 (m, 2H); 3.2 (dd, 1H); 3.4 (dq, 1H); 3.55 (m, 1H); 3.7 (m, 1H); 3.98 (dq, 1H); 4.15 (m, 2H); 7.4 (m, 1H); 7.52 (m, 1H); 7.8 (d, 1H); 7.92 (d, 1H); 8.62 (s, 1H); 8.98 (s, 1H).

(2S,4S)-1-(4-Nitrobenzyloxycarbonyl)-2-(2-carboxy-3-naphthylcarbamoyl)pyrrolidin-4-ylthioacetate.

The title compound was prepared from 3-amino-2-naphthoic acid using a similar method to that of example 8.

NMR (DMSO-$d_6$+AcOD-$d_4$+TFA-d, 100°): δ2.0–2.25 (m, 1H); 2.25 (m, 3H); 2.85 (m, 1H); 3.45 (m, 1H); 3.9–4.35 (m, 2H); 4.55 (dd, 1H); 5.25 (dd, 2H); 7.35–8.1 (m, 8H); 8.62 (s, 1H); 8.90 (s, 1H).

Allyl (1R,5R,6S,8R,2'S,4'S)-2-(1-(4-nitrobenzyloxycarbonyl)-2-(2-carboxy-3-naphthylcarbamoyl)pyrrolidin-4-ylthio)-6-(1-hydroxyethyl)-1-methylcarbapenem-3-carboxylate,(diisopropylethylamine salt).

The title compound was prepared from (2S,4S)-1-nitrobenzyloxycarbonyl-2-(2-carboxy-3-naphthylcarbamoyl)pyrrolidin-4-ylthioacetate using a similar method to that of example 8.

(1R,5R,6S,8R,2'S,4'S)-2-(1-(4-Nitrobenzyloxycarbonyl)-2-(2-carboxy- 3-napthylcarbamoyl)pyrrolidin-4-ylthio)-6-(1-hydroxyethyl)-1-methylcarbapenem-3-carboxylic acid (dipotassium salt).

The title compound was prepared from allyl (1R,5R,6S, 8R,2'S,4'S)-2-(1-(4-nitrobenzyloxycarbonyl-2-(2-carboxy-3-naphthylcarbamoyl)pyrrolidin-4-ylthio)-6-(1-hydroxyethyl)-1-methylcarbapenem-3-carboxylate (diisopropylethyl amine salt) using a similar method to that of example 8.

EXAMPLE 10

(1R,5S,6S,8R,2'S,4'S)-2-(2-(2-Methylsulfonylcarbamoyl-5-thienyl-carbamoyl)pyrrolidin-4-ylthio)-6-(1-hydroxyethyl)-1-methylcarbapenem-3-carboxylic acid (Na salt).

A solution of 4-nitrobenzyl (1R,5S,6S,8R,2'S,4'S)-2-(1-(4-nitrobenzyloxycarbonyl)-2-(2-methylsulfonylcarbamoyl-5-thienylcarbamoyl)pyrrolidin-4-ylthio)-6-(1-hydroxyethyl)-1-methylcarbapenem-3-carboxylate (0.35 g, 0.4 mmol) in water (5 ml) and sodium bicarbonate (pH adjusted to 7.5) was hydrogenated at atmospheric pressure in presence of Pd/C (10%) (175μ). The reaction was followed by analytical HPLC and took about 60 minutes. The catalyst was filtered off and the aqueous solution concentrated, and purified by preparative HPLC (Nucleosil C-18), eluting with water. Freeze drying the appropriate fractions gave the title compound (0,043g, 19%).

NMR: (DMSO-$d_6$+AcOD-$d_4$): δ1.15 (2d, 6H); 1.75 (m, 1H); 2.65 (m, 1H); 2.76 (m, 1H); 3.0 (s, 3H); 3.2 (dd, 1H); 3.34–3.48 (m, 2H); 3.64 (m, 1H); 3.92–4.04 (m, 2H); 4.16 (dd, 1H); 6.79 (d, 1H); 7.43 (d, 1H).

The starting material was prepared as follows:

5-Nitro-2-thiophenecarboxylic acid

2-Thiophenecarboxylic acid (6.4 g, 50 mM) was suspended in acetic anhydride (15 ml) and fuming nitric acid (16 ml) in glacial acetic acid (25 ml) added slowly over 1 hour with stirring, while keeping the temperature of the reaction mixture below 30° C. The reaction mixture was stirred at ambient temperature for 2 hours. The product was purified by subjecting to chromatography (470 ml) on HP20SS resin using methanol/(water+1% acetic acid): as eluant. The pure title compound was obtained together with a mixture of 4- and 5-nitrothiophene-2-carboxylic acid.

NMR (CDCl$_3$): δ7.65 (d, 1H); 7.88 (d, 1H).

Allyl 5-Nitro-2-thiophenecarboxylate

To a solution of 5-nitro-2-thiophenecarboxylic acid (20 g, 0.11 mol) in DMF (140 ml) were added sequentially allyl bromide (40 ml, 0.46 mol) and triethylamine (64 ml, 0.46 mol) with cooling to maintain the temperature of the reaction mixture below 30° C. After addition of the reagents, the reaction mixture was stirred for 3 hours at ambient temperature and then diluted with ethyl acetate. The solid which precipitated was filtered off, the filtrate washed with water, washed with saturated aqueous solution of sodium chloride, dried over MgSO$_4$ and concentrated. The residue was purified by chromatography on silica gel using a mixture of CH$_2$Cl$_2$—petroleum ether (3:7) as eluent to give the title compound as a white solid (8.8 g, 38%).

NMR (CDCl$_3$): δ4.84 (d, 2H); 5.36–5.45 (m, 2H); 6.00 (m, 1H); 7.71 (d, 1H); 7.88 (d, 1H).

Allyl 5-amino-2-thiophenecarboxylate

To a solution of allyl 5-nitro-2-thiophenecarboxylate (3.2 g, 15 mmol) in concentrated hydrogen chloride (35 ml) were added under cooling SnCl$_2$.H$_2$O (10.1 g, 45 mmol). The mixture was stirred for 3.5 hours at ambient temperature, diluted with ethyl acetate and basified to pH 10 with 5N NaOH. The organic layer was washed with water and a saturated aqueous solution of sodium chloride, dried over MgSO$_4$ and concentrated. The residue was purified by chromatography on silica gel using a mixture of ethyl acetate and petroleum ether (3:7) to give the title compound as a yellow oil (1.94 g, 72%).

NMR (CDCl$_3$): δ4.34 (br s, 2H); 4.73 (d, 2H); 5.23 (d, 1H); 5.36 (d, 1H); 5.99 (m, 1H); 6.09 (d, 1H); 7.48 (d, 1H).

(2S,4S)-1-(4-Nitrobenzyloxycarbonyl)-2-(2-allyloxycarbonyl-5-thienylcarbamoyl)pyrrolidine-4-ylthioacetate.

To a solution of (2S,4S)-4-acetylthio-2-carboxy-1-(4-nitrobenzyloxycarbonyl)pyrrolidine (3.79 g, 10.3 mmol) in CH$_2$Cl$_2$ (12 ml) were added thionyl chloride (3.75 ml, 51.5 mmol) and DMF (0.055 ml). The mixture was stirred for 16 hours at ambient temperature, concentrated and the residual oil taken up in CH$_2$Cl$_2$-toluene and reevaporated. The residue was dried under vacuum and solubilised in CH$_2$Cl$_2$ (25 ml). To this solution cooled to 0° C. was added N-diisopropylethylamine (2.05 ml, 11.8 mmol) and a solution of allyl 5-amino-2-thiophenecarboxylate (1.9 g, 10.3 mmol). After 15 minutes at ambient temperature, the solvent was evaporated and the residue taken up in a mixture of water and ethyl acetate. The organic layer was dried over MgSO$_4$ and evaporated to dryness. The residue was purified by chromatography on silica gel using a mixture of CH$_2$Cl$_2$-ether (9:1) to give the title compound as a yellow foam (4.68 g, 85%).

NMR (DMSO-$d_6$+AcOD-$d_4$): δ2.33 (s, 3H); 2.80 (m, 1H); 3.38 (m, 1H); 4.00–4.15 (m, 2H); 4.52 (m, 2H); 4.77 (d, 2H); 5.02–5.42 (m, 4H); 6.00 (m, 1H); 6.77 (m, 1H); 7.45 (m, 1H); 7.60–7.68 (m, 2H); 7.95 (m, 1H); 8.23 (m, 1H).

(2S,4S)-1-(4-Nitrobenzyloxycarbonyl)-2-(2-carboxy-5-thienylcarbamoyl)pyrrolidin-4-ylthioacetate.

A solution of (2S,4S)-1-(4-nitrobenzyloxycarbonyl)-2-(2-allyloxycarbonyl-5-thienylcarbamoyl)pyrrolidin-4-ylthioacetate (5.33 g, 10 mmol) in CH$_2$Cl$_2$ (15 ml) and ethyl acetate (15 ml) was treated with P(Ph)$_3$ (0.26 g, 1 mmol), potassium 2-ethylbenzoate (0.47M in ethyl acetate, 23.4 ml, 11 mmol) and Pd(PPh$_3$)$_4$ (0.25 g) at ambient temperature. The reaction was followed by HPLC. After 3 hours, the mixture was diluted with ethyl acetate, the precipitate filtered, washed with ether and dried. This solid was dissolved in water, acidified with HCl (2N), and the free acid extracted with ethyl acetate, dried over MgSO$_4$ and the solvent evaporated to give title compound (4.95 g, 100%).

NMR: (DMSO-d$_6$+CF$_3$CO$_2$D): δ1.95 (m, 1H); 2.33 (s, 3H); 2.78 (m, 1H); 3.38 (m, 1H); 3.98–4.1 (m, 2H); 4.52 (m, 1H); 5.03–5.33 (m, 2H); 6.72–6.76–7.52–7.54 (4d, 2H); 7.46–8.25 (4d, 4H).

(2S,4S)-1-(4-Nitrobenzyloxycarbonyl)-2-(2-methylsulfonylcarbamoyl-5-thienylcarbamoyl)pyrrolidin-4-ylthioacetate.

A solution of (2S,4S)-1-(4-nitrobenzyloxycarbonyl)-2-(2-carboxy-5-thienylcarbamoyl)pyrrolidin-4-ylthioacetate (0.75 g, 1.52 mmol) in CH$_2$Cl$_2$ (25 ml) was treated with oxalyl chloride (0.27 ml, 3.08 mmol) and DMF (20 mg). The mixture was stirred for 2 hours, evaporated, dissolved in a mixture of CH$_2$Cl$_2$: toluene 1:1 (10 ml) and evaporated. The residual oil was dried for 1 hour under vacuum and solubilized in anhydrous THF (2.5 ml). This solution was added to a solution of methylsulfonamide (0.15 g, 1.58 mmol), diisopropylethylamine (0.3 ml, 1.84 mmol) and 4-dimethylaminopyridine (0.03 g, 0.246 mmol) in anhydrous THF (5 ml) under argon. The mixture was heated at 80° C. for 2 hours and the solvent evaporated. The residue was purified by flash silica gel chromatography eluting with CH$_2$Cl$_2$: methanol (90:10) to give title compound (0.49 g, 57%).

NMR (DMSO-d$_6$+CF$_3$CO$_2$D): δ1.95 (m, 1H); 2.33 (s, 3H); 2.78 (m, 1H); 3.28–3.48 (m, 4H); 3.98–4.1 (m, 2H); 4.52 (m, 1H); 5.03–5.33 (m, 2H); 6.72–6.76–7.89–7.91 (4d, 2H); 7.45–8.24 (4d, 4H).

(2S,4S)-1-(4-Nitrobenzyloxycarbonyl)-2-(2-methylsulfonylcarbamoyl-5-carbamoyl)pyrrolidin-4-ylthiol.

(2S,4S)-1-(4-Nitrobenzyloxycarbonyl)-2-(2-methanesulfonylcarbamoyl-5-thienylcarbamoyl)pyrrolidin-4-ylthioacetate (0.475 g, 0.833 mmol) was solubilized in CH$_2$Cl$_2$ (5 ml) and dry ethanol (10 ml) and treated with a solution of methylamine (4.24 mmol) in ethanol. The progress of the reaction was monitored by tlc. After 1 hour, the soluent was evaporated to give title compound.

4-Nitrobenzyl (1R,5S,6S8R,2'S,4'S)-2-(1-nitrobenzyloxycarbonyl)-2-(2-methylsulfonylcarbamoyl-5-thienylcarbamoyl)pyrrolidin-4-ylthio)-6-(1-hydroxyethyl)-1-methylcarbapenem-3-carboxylate A solution of 4-nitrobenzyl (1R,5R,6S,8R)-6-(1-hydroxyethyl)-1-methyl-2-diphenylphosphoryloxycarbapenem-3-carboxylate (0.4 g, 0.673 mmol) in DMF (5 ml) under argon was treated with the (2S,4S)-1-(4-nitrobenzyloxycarbonyl)-2-(2-methylsulfonylcarbamoyl-5-thienylcarbamoyl)pyrrolidin-4-ylthiol from the previous step, diisopropylethylamine (0.15 ml, 0.92 mmol), tributylphosphine (0.035 ml, 0.14 mmol) and water (10 μl, 0.55 mmol), for 2 hours at ambient temperature. The mixture was then purified by subjecting to chromatography on a HP20SS column, eluting with a gradient of acetonitrile, water to give title compound (0.4 g).

NMR: (DMSO-d$_6$+AcOD-d$_4$): δ1.20 (t, 15H); 1.26 (2d, 6H); 1.93 (m, 1H); 2.81 (m, 1H); 3.02 (d, 3H); 3.15 (q, 2H); 3.31 (m, 1H); 3.37 (m, 1H); 3.54–3.6 (m, 3H); 3.92–4.06 (m, 2H); 4.11–4.33 (m, 2H); 4.50 (m, 1H); 5.05–5.46 (m, 4H); 6.60–8.30 (m, 10H).

EXAMPLE 11

(1R,5S,6S,8R,2'S,4'S)-2-(2-(2-Cyanocarbamoyl-5-thienylcarbamoyl)pyrrolidin-4-ylthio)-6-(1-hydroxyethyl)-1-methylcarbapenem-3-carboxylic acid (Na salt).

The title compound was prepared by removing the 4-nitrobenzyl protecting groups from 4-nitrobenzyl (1R,5S,6S,8R,2'S,4'S)-2-(1-(4-nitrobenzyloxycarbonyl)-2-(cyanocarbamoyl-5-thienylcarbamoyl)pyrrolidin-4-ylthio)-6-(1-hydroxyethyl)-1-methylcarbapenem-3-carboxylate using a similar method to that described in example 10.

NMR: (DMSO-d$_6$+AcOD-d$_4$): δ1.18 (2d, 6H); 1.75 (m, 1H); 2.63 (m, 1H); 2.79 (m, 1H); 3.20 (dd, 1H); 3.32–3.45 (m, 2H); 3.65 (m, 1H); 3.90–4.03 (m, 2H); 4.16 (dd, 1H); 6.61 (d, 1H); 7.21 (d, 1H).

The starting material was prepared as follows:
(2S,4S)-1-(4-Nitrobenzyloxycarbonyl)-2-(2-cyanocarbamoyl-5-thienylcarbamoyl)pyrrolidine-4-ylthioacetate.

The title compound was prepared from (2S,4S)-1-(4-nitrobenzyloxycarbonyl)-2-(2-carboxy-5-thienylcarbonyl)pyrrolidin-4-ylthioacetate by reacting with cyanamide using a similar method to that described in example 10 for the reaction of the aforementioned pyrrolidine compound with methanesulphonamide.

NMR: (DMSO-d$_6$+TFAd): δ1.95 (m, 1H); 2.33 (s, 3H); 2.79 (m, 1H); 3.39 (m, 1H); 3.95–4.18 (m, 2H); 4.56 (m, 1H); 5.02–5.35 (m, 2H); 6.78–6.85–7.79–7.84 (4d, 2H); 7.46–7.68–7.96–8.25 (4d, 4H).

4-Nitrobenzyl (1R,5R,6S,8R,2'S,4S)-2-(1-(4-nitrobenzyloxycarbonyl)-2-(2-cyanocarbamoyl-5-thienylcarbamoyl)pyrrolidin-4-ylthio)-6-(1-hydroxylethyl)-1-methylcarbapenem-3-carboxylate (diisopropylethylamine salt).

The title compound was prepared by converting the thioacetate to the thiol and reacting with 4-nitrobenzyl (1R,5R,6S,8R)-6-(1-hydroxyethyl)-1-methyl-2-diphenylphosphoryloxycarbapenem-3-carboxylate using a similar method to the described in example 10.

NMR: (DMSO-d$_6$+ACOH-d$_4$): δ1.18 (m, 15H); 1.26 (2d, 6H); 1.88 (m, 1H); 2.78 (m, 1H); 3.15 (q, 2H); 3.31 (m, 1H); 3.37 (m, 1H); 3.54–3.66 (m, 3H); 3.92–4.06 (m, 2H); 4.11–4.33 (m, 2H); 4.50 (m, 1H); 5.05–5.46 (m, 4H); 6.6–8.3 (m, 10H).

EXAMPLE 12

(1R,5S,6S,8R, 2'S,4'S)-2-(2-(3-Phenylsulfonylcarbamoylphenylcarbamoyl)pyrrolidin-4-ylthio)-6-(1-hydroxyethyl)-1-methylcarbapenem-3-carboxylic acid.

A solution of 4-nitrobenzyl (1R,5S,6S,8R,2'S,4'S)-2-(2-(3-phenylsulfonylcarbamoylphenylcarbamoyl)-1-(4-nitrobenzyloxycarbonyl)pyrrolidin-4-ylthio)-6-(1-hydroxyethyl)-1-methylcarbapenem-3-carboxylate (930 mg, 1.0 mM) in EtOAc (40 ml) was added to a suspension of 10% palladium on charcoal (150 mg) in water (30 ml) containing sodium hydrogen carbonate (84 mg, 1.0 mM). The resulting suspension was stirred in an atmosphere of hydrogen for 2 hours. The catalyst was removed by filtration through a Whatman No.50 paper. The aqueous layer was separated and partially evaporated (high vacuum & solid carbon dioxide condenser). The concentrated aqueous layer was freeze-dried overnight to give the crude title compound (550 mg) which was dissolved in a little water, sodium hydrogen carbonate (250 mg) was added, and the solution passed down a column of Diaion HP20SS resin (300×30 mm), eluting with water, then water/acetonitrile. Fractions containing the required product were combined and freeze-dried overnight to give the title compound (150 mg), which contained a little diphenylphosphoric acid.

NMR: DMSOd$_6$/CD$_3$OD 1.18–1.25 (2d, 6H); 1.95 (m, 1H); 2.87 (m, 1H); 3.17 (dd, 1H); 3.23 (dd, 1H); 3.47 (quintet, 1H); 3.68 (m, 1H); 3.91 (t, 1H); 4.01 (t, 1H); 4.20 (dd, 1H); 4.35 (t, 1H); 7.41–7.52 (m, 3H); 7.66 (dd, 1H); 7.78 (dd, 1H); 7.90 (dd, 2H); 8.22 (t, 1H). MS: FAB M$^+$659 (di Na salt), 637 (mono Na salt).

The starting material was prepared as follows:
3-Amino-N-phenylsulfonylbenzamide A solution of 3-nitro-N-phenylsulfonylbenzamide (2.6 g, 8.5 mM) in acetic acid (100 ml) containing 10% palladium on charcoal (0.5 g) was stirred under an atmosphere of hydrogen at ambient temperature and atmospheric pressure, for 15 mins. The catalyst was filtered through a Whatman No 50 filter paper and the filtrate evaporated. The resulting oil was dissolved in absolute ethanol (100 ml) and acidified with concentrated hydrochloric acid. The crystalline solid which came out overnight was collected and washed with EtOH giving 3-Amino-N-phenylsulfonylbenzamide hydrochloride as pale pink crystals (2.1 g).

Anal. Fd. C 50.2;H 4.3;N 8.8. Req. C 49.9;H 4.2;N 9.0. NMR (DMSO-d$_6$): δ7.47 (m, 2H); 7.6–7.76 (m, 5H); 8.0 (dt, 1H).

(2S,4S)-4-Acetylthio-1-(4-nitrobenzyloxycarbonyl)-2-(3-phenylsulfonylcarbamoylphenylcarbamoyl)pyrrolidine.

Di-isopropylethylamine (2.0 ml) followed by chlorotrimethylsilane (0.73 ml) was added to a stirred solution of 3-amino-N-phenylsulfonylbenzamide hydrochloride (1.8 g, 5.7 mM) in THF (distilled from CaH$_2$; 25 ml) under an argon atmosphere. The solution was allowed to stand for 30 minutes then cooled to −10 C. Meanwhile 4-acetylthio-1-(4-nitrobenzyloxycarbonyl)-2-carboxypyrrolidine (1.84 g, 5 mM) dissolved in tetrahydrofuran (25 ml) was treated with N-methylmorpholine (1.1 ml, 10 mM). This solution was cooled to −15° C. with stirring under an argon atmosphere, and treated with isobutyl chloroformate (0.66 ml, 5 mM) in one portion. After 20 minutes, this solution was added to the solution of the trimethylsilyl derivative of the aniline (prepared above). When the addition was complete, the mixture was stirred for 15 minutes and the solvent evaporated. The residue was partitioned between ethyl acetate (200 ml) and 1M aqueous hydrochloric acid (100 ml). The ethyl acetate layer was washed with hydrochloric acid, brine and dried giving (2S,4S)-4-acetylthio-1-(4-nitrobenzyloxycarbonyl)-2-(3-phenylsulfonylcarbamoylphenylcarbamoyl)pyrrolidine as a gum which was crystallised from EtOH (2.3 g).

NMR (DMSO-d$_6$): 1.93 (m, 1H); 2.31 (s, 3H); 2.80 (m, 1H); 3.33 (m, 2H); 4.05 (m, 2H); 4.46 (m, 1H); 5.05–5.30 (m, 2H); 7.35–8.30 (complex pattern of doublets and multiplets, 9H).

4-Nitrobenzyl-(1R,5S,6S,8R,2'S,4'S)-2-(2-(3-phenylsulfonylcarbamoylphenylcarbamoyl)-1-(4-nitrobenzyloxycarbonyl)pyrrolidin-4-ylthio)-6-(1-hydroxyethyl)-1-methylcarbapenem-3-carboxylate The method was the same as in example 6 except that (2S,4S)-4-acetylthio-1-(4-nitrobenyloxycarbonyl-2-(3-phenylsulfonylcarbamoylphenylcarbamoyl)pyrrolidin (0.94 g, 1.5 mM) was used. The crude product (1.9 g) was subjected to chromatography on silica gel (Merck 9385, column 40 mm diameter filled to a depth of 120 mm), eluting with a gradient of dichloromethane and methanol. Fractions containing the required product were combined and evaporated giving the title compound as a white solid (1 g).

NMR (CD$_3$COOD-DMSO-d$_6$): 1.17 (m, 6H), 1.90 (m, 1H), 2.80 (m, 1H); 3.26 (dd, 1H); 3.34 (m, 1H); 3.48–3.61 (m, 1H); 3.85–4.20 (m, 3H); 4.25 (broad d, 1H); 4.42 (m, 1H); 5.13 (dd, 2H), 5.32 (dd, 2H); 7.21–8.22 (complex pattern of doublets, double doublets and multiplets, 17H).

We claim:

1. A compound of the formula (I):

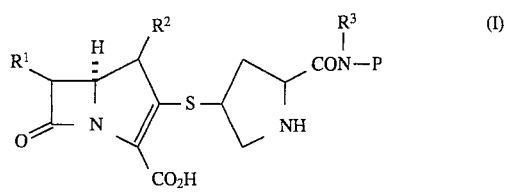

or a pharmaceutically acceptable salt or in vivo hydrolysable ester thereof wherein:

$R^1$ is 1-hydroxyethyl, 1-fluoroethyl or hydroxymethyl;

$R^2$ is hydrogen or $C_{1-4}$alkyl;

$R^3$ is hydrogen or $C_{1-4}$alkyl;

P is of the formula (IA), (IB) or (IC)

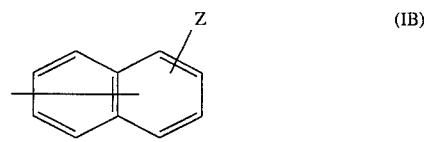

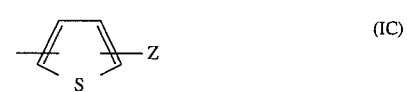

and the formula (IB) the naphthyl group may be bonded to the nitrogen of the linking carbamoyl group at either ring;

Z is carboxy, sulfonic acid, sulfonic acid, $C_{1-4}$alkanamidosulfonyl (—SO$_2$NHCOC$_{1-3}$alkyl), benzamidosulfonyl, $C_{1-4}$alkylsulfonylcarbamoyl (—CONHSO$_2$C$_{1-4}$alkyl), phenylsulfonylcarbamoyl, $C_{1-4}$alkoxycarbamoyl, hydroxycarbamoyl, sulfoamino, N-$C_{1-4}$alkanesulfonamido, cyanocarbamoyl, cyanosulfamoyl, tetrazol-5-yl, 3-hydroxyisoxazol-4-yl or 3-hydroxyisoxazol-5-yl;

and P is optionally further substituted by one or two substituents selected from halo, cyano, $C_{1-4}$alkyl, nitro, hydroxy, carboxy, $C_{1-4}$alkoxy, trifluoromethyl, $C_{1-4}$alkoxycarbonyl, amino, $C_{1-4}$alkylamino, di-$C_{1-4}$alkylamino, sulfonic acid, $C_{1-4}$alkylS(O)$_n$- wherein n is 0–2, $C_{1-4}$alkanoylamino, $C_{1-4}$alkanoyl(N-$C_{1-4}$alkyl)amino, carbamoyl, $C_{1-4}$alkylcarbamoyl and di-$C_{1-4}$alkylcarbamoyl;

provided that when P is a ring of the formula (IA) or (IC) and Z is either sulfonic acid or N-$C_{1-4}$alkanesulfonamido, the ring is not further substituted by carboxy; and when P is of the formula (IA) or (IC), Z is not carboxy.

2. The compound according to claim 1 wherein $R^1$ is 1-hydroxyethyl and $R^2$ is methyl.

3. The compound according to either claim 1 or claim 2 of the formula (IV):

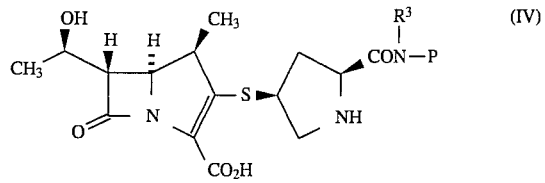

wherein P, $R^3$, and optional substituents on P are as defined in claim 1.

4. The compound according to claim 1 which is (1R,5S,6S,8R,2'S,4'S)-2-(2-(3-sulfophenylcarbamoyl)pyrrolidin-4 -ylthio)-6-(1-hydroxyethyl)-1-methylcarbapenem-3-carboxylic acid;

(1R,5S,6S,8R,2'S,4'S)-2-(2-(3-methylsulfonylcarbamoylphenylcarbamoyl) pyrrolidin-4-ylthio)-6-(1-hydroxyethyl)-1-methylcarbapenem-3-carboxylic acid;

(1R,5S,6,S,8R,2'S,4'S)-2-(2-(2-(3-1H-tetrazol-5-yl)phenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-hydroxy-5-sulfophenylcarbamoyl) pyrrolidin-4-ylthio)-6-(1-hydroxyethyl)-1-methylcarbapenem-3-carboxylic acid;

(1R,5S,6S,8R,2'S,4'S)-2-(2-(2-methoxy-5-methyl-4-sulfophenylcarbamoyl) pyrrolidin-4-ylthio)-6-(1-hydroxyethyl)-1-methylcarbapenem-3-carboxylic acid;

(1R,5S,6S,8R,2'S,4'S)-2-(2-(3-phenylsulfonylcarbamoylphenylcarbamoyl) pyrrolidin-4-ylthio)-6-(1-hydroxyethyl)-1-methylcarbapenem-3-carboxylic acid;

(1R,5S,6S,8R,2'S,4'S)-2-(2-(2-methylsulfonylcarbamoyl-5-thienyl carbamoyl)pyrrolidin-4-ylthio)-6-(1-hydroxyethyl)-1-methylcarbapenem-3-carboxylic acid;

(1R,5S,6S,8R,2'S,4'S)-2-(2-(2-cyanocarbamoyl-5-thienylcarbamoyl) pyrrolidin-4-ylthio)-6-(1-hydroxyethyl)-1-methylcarbapenem-3-carboxylic acid;

(1R,5S,6S,8R,2'S,4'S)-2-(2-(2-sulfo-5-thienylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(1-carboxy-3-naphthylcarbamoyl)pyrrolidin-4-ylthio)-6(1-hydroxyethyl)-1-methylcarbapenem-3-carboxylic acid;

(1R,5S,6S,8R,2'S,4'S)-2-(2-(2-carboxy-3-naphthylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-sulfophenylcarbamoyl)pyrrolidin-4-ylthio)-6-(1-hydroxyethyl)-1-methylcarbapenem-3-carboxylic acid; or (1R,5S,6S,8R,2'S,4'S)-2-(2-(2-hydroxy-4-sulfo-1-naphthylcarbamoyl) pyrrolidin-4-ylthio)-6-(1-hydroxyethyl)-1-methylcarbapenem-3-carboxylic acid;

or a pharmaceutically acceptable salt thereof.

5. The compound according to claim 1 wherein ring P is of the formula (IA).

6. The compound according to claim 5 wherein substituent Z on ring P is sulfonic acid, tetrazol-5-yl, $C_{1-4}$alkysulfonylcarbamoyl, phenylsulfonylcarbamoyl or cyanocarbamoyl.

7. The compound according to claim 5 or 6 wherein optional substituents on P are selected from halo, cyano, $C_{1-4}$alkyl, nitro, hydroxy, $C_{1-4}$alkoxy, carbamoyl, amino and trifluoromethyl.

8. The compound according to claim 1 wherein ring P is of the formula (IB).

9. The compound according to claim 8 wherein substituent Z on ring P is carboxy.

10. The compound according to claim 8 wherein substituent Z on ring P is sulfonic acid, tetrazol-5-yl, $C_{1-4}$alkysulfonylcarbamoyl, phenylsulfonylcarbamoyl or cyanocarbamoyl.

11. The compound according to claim 8, 9 or 10 wherein optional substituents on P are selected from halo, cyano, $C_{1-4}$alkyl, nitro, hydroxy, $C_{1-4}$alkoxy, carbamoyl, amino and trifluoromethyl.

12. The compound according to claim 1 wherein ring P is of the formula (IC).

13. The compound according to claim 12 wherein substituent Z on ring P is sulfonic acid, tetrazol-5-yl, $C_{1-4}$alkysulfonylcarbamoyl, phenylsulfonylcarbamoyl or cyanocarbamoyl.

14. The compound according to claim claim 12 or 13 wherein optional substituents on P are selected from halo, cyano, $C_{1-4}$alkyl, nitro, hydroxy, $C_{1-4}$alkoxy, carbamoyl, amino and trifluoromethyl.

15. A pharmaceutical composition which comprises a pharmaceutically effective amount of the compound according to claim 1 and a pharmaceutically acceptable carrier.

16. A pharmaceutical composition which comprises a pharmaceutically effective amount of the compound according to claim 2 and a pharmaceutically acceptable carrier.

17. A pharmaceutical composition which comprises a pharmaceutically effective amount of the compound according to claim 3 and a pharmaceutically acceptable carrier.

18. A pharmaceutical composition which comprises a pharmaceutically effective amount of the compound according to claim 4 and a pharmaceutically acceptable carrier.

19. A pharmaceutical composition which comprises a pharmaceutically effective amount of the compound according to claim 5 and a pharmaceutically acceptable carrier.

20. A pharmaceutical composition which comprises a pharmaceutically effective amount of the compound according to claim 6 and a pharmaceutically acceptable carrier.

21. A pharmaceutical composition which comprises a pharmaceutically effective amount of the compound according to claim 7 and a pharmaceutically acceptable carrier.

22. A pharmaceutical composition which comprises a pharmaceutically effective amount of the compound according to claim 8 and a pharmaceutically acceptable carrier.

23. A pharmaceutical composition which comprises a pharmaceutically effective amount of the compound according to claim 9 and a pharmaceutically acceptable carrier.

24. A pharmaceutical composition which comprises a pharmaceutically effective amount of the compound according to claim 10 and a pharmaceutically acceptable carrier.

25. A pharmaceutical composition which comprises a pharmaceutically effective amount of the compound according to claim 11 and a pharmaceutically acceptable carrier.

26. A pharmaceutical composition which comprises a pharmaceutically effective amount of the compound according to claim 12 and a pharmaceutically acceptable carrier.

27. A pharmaceutical composition which comprises a pharmaceutically effective amount of the compound according to claim 13 and a pharmaceutically acceptable carrier.

28. A pharmaceutical composition which comprises a pharmaceutically effective amount of the compound according to claim 14 and a pharmaceutically acceptable carrier.

29. A method of treating a bacterial infection in a mammal by administering an antibacterially effective amount of the compound according to claim 1 to said mammal in need thereof.

30. A method of treating a bacterial infection in a mammal by administering an antibacterially effective amount of the compound according to claim 2 to said mammal in need thereof.

31. A method of treating a bacterial infection in a mammal by administering an antibacterially effective amount of the compound according to claim 3 to said mammal in need thereof.

32. A method of treating a bacterial infection in a mammal by administering an antibacterially effective amount of the compound according to claim 4 to said mammal in need thereof.

33. A method of treating a bacterial infection in a mammal by administering an antibacterially effective amount of the compound according to claim 5 to said mammal in need thereof.

34. A method of treating a bacterial infection in a mammal by administering an antibacterially effective amount of the compound according to claim 6 to said mammal in need thereof.

35. A method of treating a bacterial infection in a mammal by administering an antibacterially effective amount of the compound according to claim 7 to said mammal in need thereof.

36. A method of treating a bacterial infection in a mammal by administering an antibacterially effective amount of the compound according to claim 8 to said mammal in need thereof.

37. A method of treating a bacterial infection in a mammal by administering an antibacterially effective amount of the compound according to claim 9 to said mammal in need thereof.

38. A method of treating a bacterial infection in a mammal by administering an antibacterially effective amount of the compound according to claim 10 to said mammal in need thereof.

39. A method of treating a bacterial infection in a mammal by administering an antibacterially effective amount of the compound according to claim 11 to said mammal in need thereof.

40. A method of treating a bacterial infection in a mammal by administering an antibacterially effective amount of the compound according to claim 12 to said mammal in need thereof.

41. A method of treating a bacterial infection in a mammal by administering an antibacterially effective amount of the compound according to claim 13 to said mammal in need thereof.

42. A method of treating a bacterial infection in a mammal by administering an antibacterially effective amount of the compound according to claim 14 to said mammal in need thereof.

\* \* \* \* \*